United States Patent
Stamler et al.

(10) Patent No.: US 6,359,182 B1
(45) Date of Patent: Mar. 19, 2002

(54) C-NITROSO COMPOUNDS AND USE THEREOF

(75) Inventors: Jonathan S. Stamler, Chapel Hill; Eric J. Toone, Durham, both of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/695,934

(22) Filed: Oct. 26, 2000

(51) Int. Cl.[7] .................. C07D 211/90; C07D 405/14; C07D 413/04; C07D 231/12; A61P 29/00
(52) U.S. Cl. .................. 568/949; 564/300; 564/301; 558/480; 558/488; 534/568
(58) Field of Search .................. 568/949; 534/568; 564/300, 301; 558/480, 488

(56) References Cited

PUBLICATIONS

Feelisch, M. and Stamler, J. S., Methods in Nitric Oxide Research, John Wiley & Sons, New York, 1996, p. 92.
Sklyar, Yu. E., et al., Khimiya Geterotsiklicheskikh Soedinenii, vol. 5, No. 1, pp. 70–73 (1969).
Rehse, K., et al., Arch. Pharm. Pharm. Med. Chem. 331, 79–84 (1998).
Rehse, K., et al., Arch. Pharm. Pharm. Med. Chem. 331, 104–110 (1998).
Ansari et al. Indian Journal of Chemistry, vol. 27B, Apr. 1988, pp. 355–357).*
Zbiral et al. Tetrahedron, 24 (3), 1363–76, 1968.*
Aktaev et al. Chem. Abstract vol. 83, 1975 p. 457 (27640j).*

* cited by examiner

Primary Examiner—Mark Berch
Assistant Examiner—Kahsay Habte

(57) ABSTRACT

A C-nitroso compound having a molecular weight ranging from about 225 to about 1,000 (from about 225 to about 600 for oral administration) on a monomeric basis wherein a nitroso group is attached to a tertiary carbon, which is obtained by nitrosylation of a carbon acid having a pKa less than about 25, is useful as an NO donor. When the compound is obtained from a carbon acid with a pKa less than about 10, it provides vascular relaxing effect when used at micromolar concentrations and this activity is potentiated by glutathione to be obtained at nanomolar concentrations. When the compound is obtained from a carbon acid with a pKa ranging from about 15 to about 20, vascular relaxing effect is obtained at nanomolar concentrations without glutathione. The compound is preferably water-soluble and preferably contains a carbon alpha to the nitrosylated carbon which is part of a ketone group. In one embodiment, the C-nitroso compound is obtained by nitrosylation of a conventional drug or such drug modified to modify the carbon acid pKa thereof When such drug is a nonsteroidal anti-inflammatory drug, the resulting C-nitroso compound functions as a COX-1 and COX-2 inhibitor without the deleterious effects associated with COX-1 inhibition but with the advantageous effects associated with COX-1 and COX-2 inhibition. One such C-nitroso compound is a nitrosoketoibuprofen. A specific example of this kind of compound is isolated as dimeric 2-[4'-(α-nitroso)isobutyrylphenyl] propionic acid. In another case, the C-nitroso compound contains the moiety

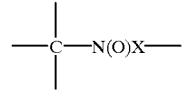

where X is S, O or NR One embodiment is directed to COX-2 inhibitors where a tertiary carbon atom and/or an oxygen atom and/or a sulfur atom is nitrosylated.

19 Claims, 3 Drawing Sheets

C-NITROSO COMPOUNDS AND USE THEREOF

TECHNICAL FIELD

The invention relates to C-nitroso compounds which are therapeutically active at low concentrations as NO donors.

BACKGROUND OF THE INVENTION

NO donors are known to be useful for therapeutic utility, e.g., to prevent restenosis following angioplasty (Groves, P., et al., Cardiovascular Research 26, 615–619 (1992)), to inhibit platelets to prevent coagulation and thrombus formation (Groves, P., et al., Circulation 87, 590–597 (1993)) and to treat angina (Knight, et al., Circulation 95, 125–132 (1997)). NO donors are considered to have additional therapeutic utility in cancer, killing microbes and viruses, relaxing airways and intestinal smooth muscle (e.g., for treating asthma and esophageal spasms), in promoting erectile function and in treatment of heart failure and urinary incontinence.

NO donors are described in "Methods in Nitric Oxide Research," edited by Feelisch, M., and Starnler, J. S., John Wiley & Sons, New York, 1996 at pages 71–115. These NO donors are O-nitroso and S-nitroso compounds, and C-nitroso compounds that are excluded from the invention herein.

Twenty-two additional C-nitroso compounds are described in Rehse, K., et al., Arch. Pharm. Pharm. Med. Chem. 331, 104–110 (1998). These compounds are of low molecular weight and are not water-soluble and were shown to be weakly active. Other C-nitroso compounds are described in Rehse, K, et al., Arch. Pharm. Pharm. Med. Chem. 331, 79–84 (1998); these are nitro-nitroso compounds and the specific compounds mentioned are excluded from the invention herein.

Other C-nitroso compounds which are old are 3-methyl-3-nitroso-2,4-pentanedione and 5 3-ethyl-3-nitroso-2,4-pentanedione. These compounds and their synthesis are described in Sklyar, Yu. E., et al., Khimiya Geterotsiklicheskikh Soedinenii 5, 70–73 (1969). These compounds are of low molecular weight and do not meet the definition of water solubility set forth hereinafter.

SUMMARY OF THE INVENTION

It has been discovered in a first embodiment herein that certain C-nitroso compounds of higher molecular weight than have previously been prepared, especially those that are water-soluble, are therapeutically active as NO donors at nanomolar concentrations, in some cases when used alone and in some cases in the presence of glutathione.

The C-nitroso compounds of the first embodiment herein have a nitroso group attached to a tertiary carbon. Otherwise there is an essentially irreversible tautomerization to the corresponding oxime which is generally not active. It has been discovered herein that the nitroso group being attached to a tertiary carbon is important for good activity.

The C-nitroso compounds of the first embodiment herein have a molecular weight ranging from about 225 to about 1,000 on a monomeric basis. The high activity obtained for compounds of this molecular weight is considered to be surprising and means that many drugs that are now being used can be converted to C-nitroso compounds providing not only the therapeutic effect of the starting drug but also advantages provided by nitroso group including relaxation effect and other advantages as described later.

The C-nitroso compounds of the first embodiment herein are obtained by nitrosylation of a carbon acid having a pKa less than about 25. C-nitroso compounds derived from carbon acids with lower acidities (higher pKa values) will not act as useful donors of NO.

Thus, the invention of the first embodiment in its broad aspects is directed to a C-nitroso compound having a molecular weight ranging from about 225 to about 1,000 on a monomer basis wherein a nitroso group is attached to a tertiary carbon, which is obtained by nitrosylation of a carbon acid having a pKa less than about 25.

The C-nitroso compound is preferably water-soluble and preferably contains carbon alpha to nitrosylated carbon which is part of a ketone group.

In one subgenus, the C-nitroso compound is obtained by nitrosylation of a carbon acid having a pKa less than 10. Compounds of this subgenus, when used alone, have NO donating and relaxation providing activity when used at micromolar concentrations. However, it has been discovered herein that this activity is potentiated by glutathione, so compounds of this subgenus, when administered with or to react with glutathione, are therapeutically active (to provide NO donating and relaxation effects) when used at nanomolar concentrations. Thus, an embodiment herein is directed to a method of treating a patient with such C-nitroso compound at nanomolar (e.g., from 0.1 to 900 nanomolar) concentrations, together with glutathione to provide NO donating and relaxing effect, where the patient is one in need of NO donating and/or relaxing effect and/or is in need of nitrosoglutathione.

In another subgenus, the C-nitroso compound is obtained by nitrosylation of a carbon acid having a pKa ranging from about 15 to about 20. It has been found in this case that the compound is therapeutically active and provides nitrosylating activity and relaxing effect when used at nanomolar concentrations without potentiation and that glutathione inhibits the activity of the compound.

It has been discovered herein that C-nitroso compounds of the invention herein can be obtained by nitrosylating the tertiary carbon atom of a conventional drug if that drug constitutes a carbon acid having a pKa less than 25 or can be converted to a carbon acid having a pKa less than 25 and will provide a C-nitroso compound meeting the afore-described molecular weight limitations. The resulting C-nitroso compounds retain the activity of the drug and additionally provide the relaxation effect associated with NO and can provide other beneficial effect as described below.

It has been discovered herein that when the conventional drug is a nonsteroidal anti-inflammatory drug that is a COX-1 and a COX-2 inhibitor, the resulting C-nitroso compound will function as a COX-1 and COX-2 inhibitor without the deleterious effects associated with COX-1 inhibition but with the advantages associated with COX-1 and COX-2 inhibition. In particular, COX-1 mediates production of thromboxane which mediates platelet aggregation thereby providing a deleterious deletions effect; inhibition of COX-1 reverses this effect. This reversal is reinforced by the C-nitroso nonsteroidal anti-inflammatory drugs herein. On the other hand, COX-1 inhibitors inhibit production of prostaglandins which protect against ulcers; the NO associated with the nonsteroidal anti-inflammatory drugs herein protects against this deleterious side effect. While the COX-1 inhibiting effect that mediates stomach attack is partly related to a deficiency of NO, there is an NO beneficial effect that may be COX-1 independent that more than negates the detrimental effect of inhibition of COX-1 production of prostaglandins. Thus, the C-nitroso nonsteroidal anti-inflammatory COX-1/COX-2 inhibitors herein provide an advantage over selective inhibitors of COX-2 in also providing the advantageous effects associated with COX-1 inhibition and other NO beneficial effects. Furthermore, C-nitroso selective COX-2 inhibitors provide not only the advantages of COX-2 inhibition but also some of the advantages associated with COX-1 inhibition. Furthermore, the NO in C-nitroso COX inhibitors potentiates the alleviating effect of COX inhibitors on urinary incontinence.

Dimeric 2-[4'-(α-nitroso)isobutyrylphenyl]propionic acid has been synthesized herein and is obtained by C-nitrosylation of ibuprofen modified to have a lower carbon acid pKa. It represents a C-nitroso compound herein obtained by nitrosylation of a carbon acid having a pKa ranging from about 15 to about 25 and is therapeutically active without glutathione when used at nanomolar concentrations Thus, one embodiment herein is directed to a method of treating a patient with an inflammatory or painful disorder comprising administering to said patient a therapeutically effective (inflammation and/or pain relieving) amount of a C-nitroso compound of the instant invention which is obtained by nitrosylation of the tertiary carbon of a conventional nonsteroidal anti-inflammatory drug which has a carbon acid pKa ranging from about 15 to about 20 or such modified to have this carbon acid pKa where the C-nitroso compound preferably is dimeric 2-[4'-(α-nitroso) isobutyrylphenyl]propionic acid or an aqueous solution thereof.

It has also discovered herein that the pKa of a carbon acid of a compound may be used to target an NO group to provide nitrosylated compound. This is not the case in preparing other classes of NO donor, e.g., -ONO and -SNO NO donors.

In addition, there has been discovered a new class of compounds, that are C-nitroso compounds and contain the moiety

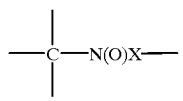

where X is S, O or NR and protonated derivatives thereof which are useful in promoting compound lifetime and providing modulated bioactivity. These compounds have a molecular weight ranging, for example, from about 100 to about 1,000 on a monomeric basis. These compounds are referred to as C-nitroso compounds of the second embodiment herein. The compounds of Rehse, K. et al., Arch. Pharm. Pharm. Med. Chem. 331, 79–84 (1998) are excluded from the new class of compounds herein.

Shinmura, K, et al., PNAS 97, 10197–10202 (2000) shows COX-2 mediates cardioprotective effects of ischemic preconditioning, in particular the late phase of ischemic preconditioning (in this case the heart is made ischemic briefly to protect against a subsequent ischemia that is much more severe). Thus COX-2 inhibitors interfere with this cardioprotective effect. However, in the case of C-nitroso COX-2 inhibitors herein the NO replaces the COX-2 mediation that is lost so there is a special benefit. This is also a similar benefit obtained with O-nitroso and S-nitroso COX-2 inhibitors. Thus, one embodiment herein is directed to COX-2 inhibitors where a tertiary carbon or an oxygen or sulfur is nitrosylated.

As used herein, the term "carbon acid" means compound that contains a CH group which disassociates to C$^-$ and H$^+$.

As used herein, the term "water-soluble" means dissolves in water at least to provide a concentration of 1 micromolar.

As used herein, the term "conventional drug" means therapeutic agent without NO donor effect.

BRIEF DESCRIPTION OF THE DRAWINGS

FIG. 1 is directed results with compound (129a) described hereinafter.

FIG. 2 is directed to results with C-nitroso-methylmalonic acid.

FIG. 3 is directed to result with C-nitrosobenzene.

FIG. 4 is directed to results with C-nitrosophenol.

FIG. 5 is directed to results with the C-nitrosoketoibuprofen synthesized in Example I.

FIG. 6 is similar to FIG. 5 but with indications of presence of dimer and more denotations of concentration.

FIG. 7 is directed to results for the combination of the C-nitrosoketoibuprofen and 100 μM glutathione.

FIG. 8 similar to FIG. 5 but with another concentration denoted.

FIG. 9 is directed to results for 3-methyl-3-nitroso-2,4-pentanedione, including potentiation with glutathione (GSH).

FIG. 10 is directed to results for 2-methyl-2-nitrosopropane.

FIGS. 2, 3, 4, 9 and 10 are directed to results with reference compounds although FIG. 9 is relied on for showing the potentiation effect that occurs in one embodiment of the invention.

FIGS. 1 and 5–8 are directed to results with C-nitroso compound of embodiments of the invention.

DETAILED DESCRIPTION

Figure 1:
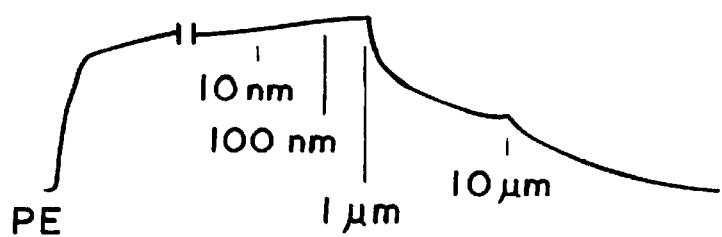
FIGS. 1–10 are tracings of tension (force) versus time with concentrations of compound also shown for particular times and show results of Example II.

We turn now to the embodiment of the invention directed to a C-nitroso compound having a molecular weight ranging from about 225 to about 1,000 on a monomer basis wherein a nitroso group is attached to a tertiary carbon which is obtained by nitrosylation of a carbon acid having a pKa less than about 25. The molecular weight typically ranges from about 225 to about 600 on a monomer basis for oral administration.

We turn now to the subgenus where the C-nitroso compound is obtained by nitrosylation of a carbon acid having a pKa less than about 10. When used alone, this compound displays activity (NO donating and/or relaxation activity) when used at micromolar concentrations and will nitrosylate the modestly nucleophilic thiol of a cysteine residue or a low molecular weight derivative (e.g., glutathione). The native activity is presumably mediated by nitrite derived from nitrosylation of water. This mode of action shows little if any specificity and is very weak. As indicated above, it has been discovered in the course of this invention that this activity is potentiated by the presence of glutathione. This potentiation is roughly 1,000-fold.

We turn now to the subgenus where the C-nitroso compound is obtained by nitrosylation of a carbon acid having a pKa ranging from about 15 to about 20. These C-nitrosothiols will not nitrosylate glutathione but will selectively nitrosylate highly nucleophilic thiols found in protein targets. Thus, highly nucleophilic thiols can be targeted by the use of these C-nitroso compounds.

The C-nitroso compounds described in "Methods in Nitric Oxide Research," edited by Feelisch, M. and Stamler, J. S., John Wilen & Sons, New York (1996) are excluded from the invention herein.

The C-nitroso compounds described in Rehse, K., et al., Arch. Pharm. Pharm. Med. Chem. 331, 104–110 (1998) and Rehse, K, et al., Arch. Pharm. Pharm. Med. Chent, 331, 79–84 (1998) are excluded from the C-nitrosothiols of the invention.

Also excluded from the C-nitrosothiols of the invention are the C-nitrosodiones described in Sklyar, Yu. E., et al., Khimiya Geterotsiklicheskikh Soedinenii 5,70–73 (1969).

The potentiation effect of glutathione on C-nitroso compounds derived from carbon acids with pKa's less than 10 is new and is one embodiment of the invention herein.

The C-nitrosylated compounds herein, when isolated, form dimers which are solid and very stable and therefore the compounds herein have long shelf lives and are capable of being stored at ambient temperatures in the presence of oxygen and light for months. While the dimers are inactive, they form monomers in water which are active. They can be administered as aqueous solutions for instant activity. They also can be administered as dimers to provide sustained release effect as the dimer dissolves in the body. Thus, the dimers herein have been discovered to promote compound lifetime and modulate compound bioactivity, and the release rates are not directly related to the activity of these compounds. The dimerization and greater stability are greatly favored for α-acyl C-nitroso compounds; hence the preference above for C-nitroso compounds where carbon alpha to the nitrosylated carbon is part of a ketone group.

As indicated above, C-nitroso compound herein is obtained by nitrosylating a tertiary carbon atom of a conventional drug or of a conventional drug modified to modify the carbon acid pKa thereof The carbon acid pKa can be reduced, for example, by converting a carbon alpha to tertiary carbon to be nitrosylated to a ketone group or by the addition of other electron withdrawing substituent (e.g., fluorine, nitro or cyanide).

When C-nitroso compound is obtained from a conventional drug, it retains the functionality of the drug and also provides NO donating relaxing effect. Sometimes this results in a synergistic effect. For example, when the C-nitroso compound is derived from a nonsteroidal anti-inflammatory drug which inhibits COX-1 as well as COX-2, the result is a COX-1 inhibitor with the advantages but not the disadvantages of COX-1 inhibition by conventional NSAIDS and also a COX-2 inhibitor with the advantages thereof and wherein certain beneficial effects (e.g., amelioration of urinary incontinence or mediating preconditioning) may be potentiated or newly endowed. A compound synthesized herein was derived from ibuprofen which inhibits COX-1 as well as COX-2. In the synthesis, the ibuprofen was first converted to ketoibuprofen to lower the pKa to be within 15 to 20. The nitrosylated compound, a nitrosoketoibuprofen, isolated as dimeric 2-[4'-(α-nitroso) isobutyrylphenyl]propionic acid, provides the advantages of COX-1 and COX-2 inhibition without pathological effects typically associated with COX-1 inhibition.

Below are listed conventional drugs and C-nitroso compounds of the first embodiment of the invention derived therefrom.

The analgesic acetylsalicylic acid has the formula

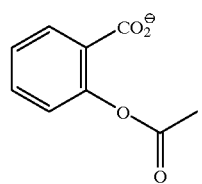

C-Nitroso compounds of the invention derived from acetylsalicylic acid include, for example:

(1)

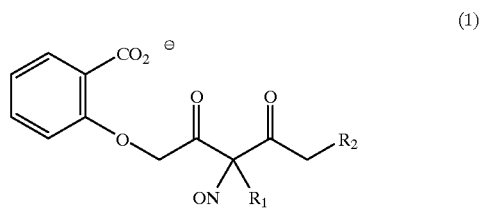

(2)

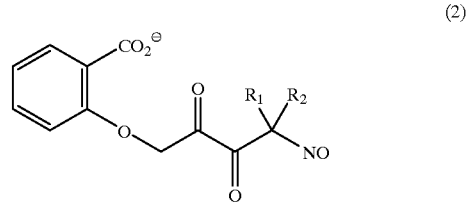

(3)

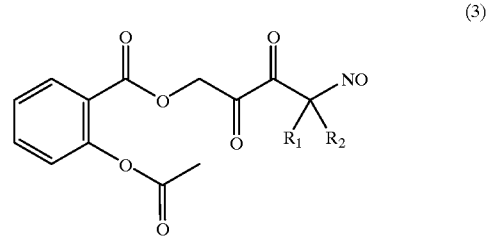

In (1), (2) and (3), $R_1$, and $R_2$ are selected from the group consisting of $C_1$–$C_6$ alkyl and $C_6$–$C_{20}$ aryl and substituted derivatives of these, e.g., substituted with amino, hydroxyl and/or carboxy and/or which are sulfated and/or phosphorylated .

The antianginal propanalol has the formula:

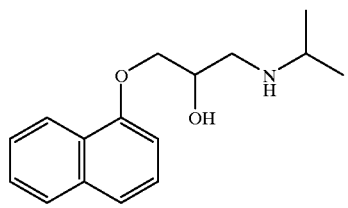

C-Nitroso compounds of the invention derived from propanalol include, for example:

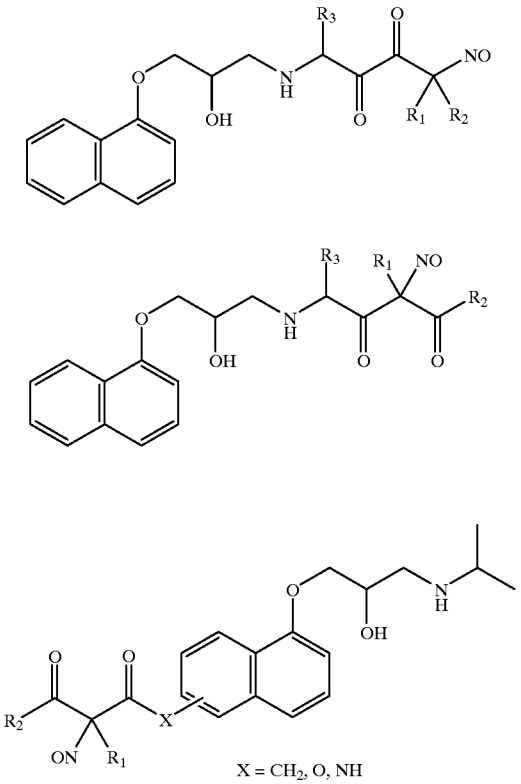

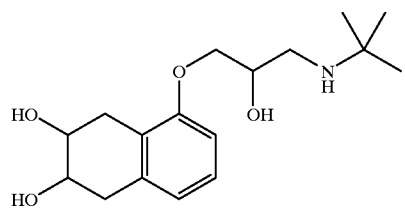

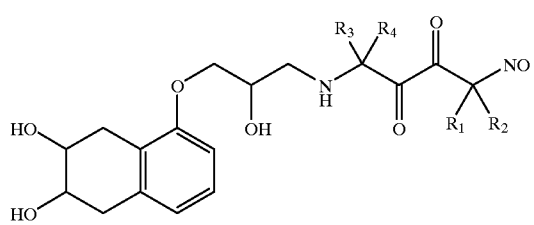

In (4), (5) and (6), $R_1$, $R_2$ and $R_3$ are selected from the group consisting of $C_1$–$C_6$ alkyl and $C_6$–$C_{20}$ aryl and substituted derivatives of these, e.g., substituted with amino, hydroxyl and/or carboxy and/or which are sulfated and/or phosphorylated.

The antianginal nadolol has the formula:

C-Nitroso compounds of the invention derived from nadolol include, for example:

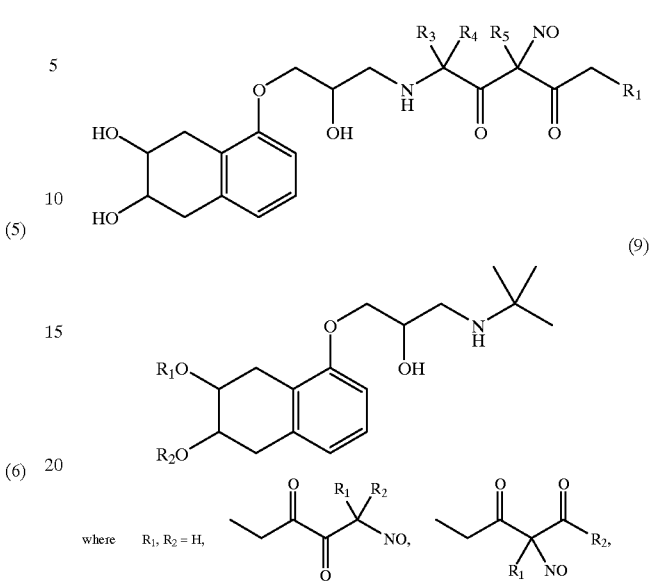

In (7), (8) and (9), $R_1$, $R_2$, $R_3$, $R_4$ and $R_5$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antianginal and heart failure protective carvedilol has the formula:

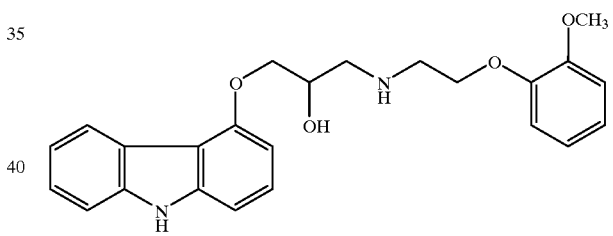

C-Nitroso compounds of the invention derived from carvedilol include, for example:

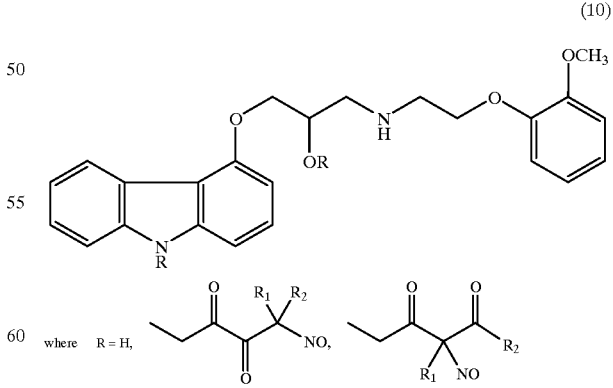

In (10), $R_1$ and $R_2$ are selected from group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antihypertensive prazosin has the formula:

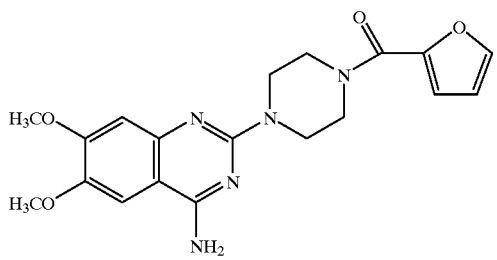

C-Nitroso compounds of the invention derived from prazosin which are exemplary of alpha adrenergic receptor agonists useful to treat erectile dysfunction, include, for example:

(11)

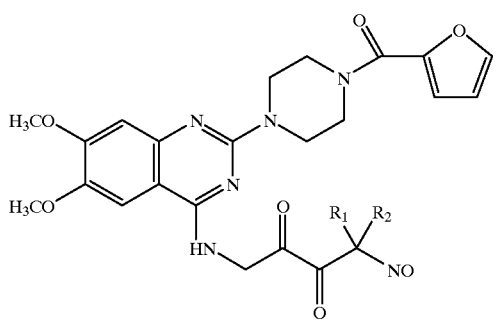

(12)

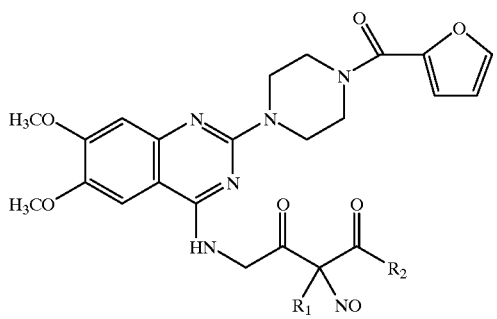

(13)

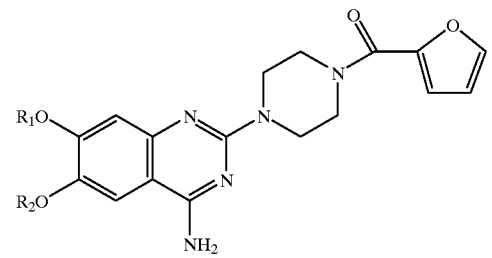

where $R_1, R_2 = CH_3$,

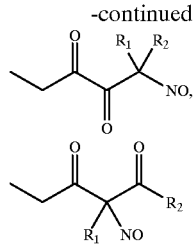

-continued

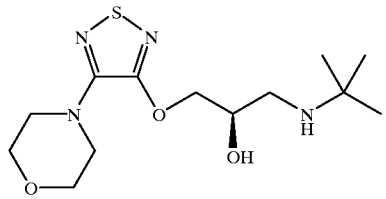

In (11), (12) and (13), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antihypertensive tinolol has the formula:

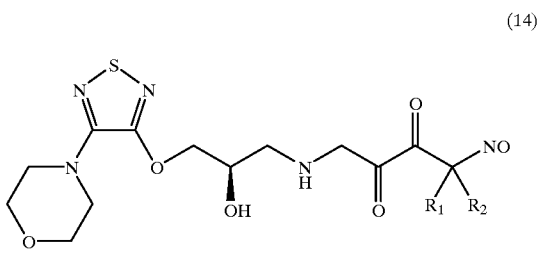

C-Nitroso compounds of the invention derived from tinolol include, for example:

(14)

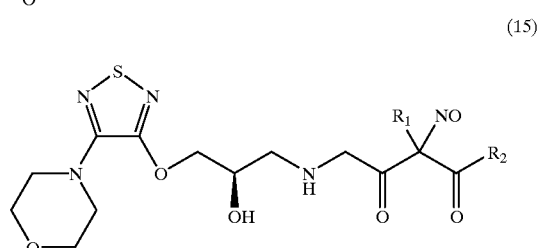

(15)

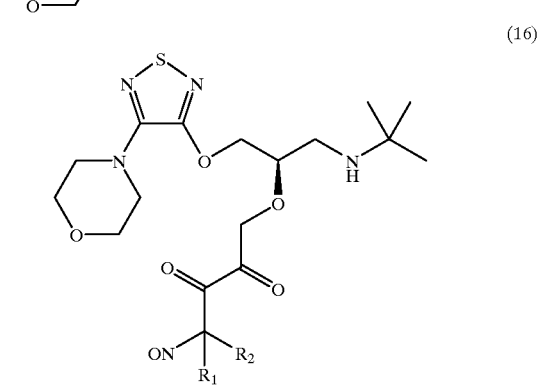

(16)

(17)
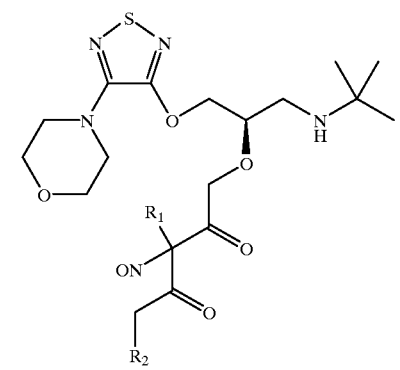

(18)
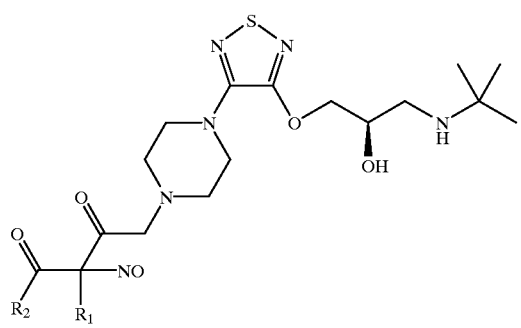

(19)
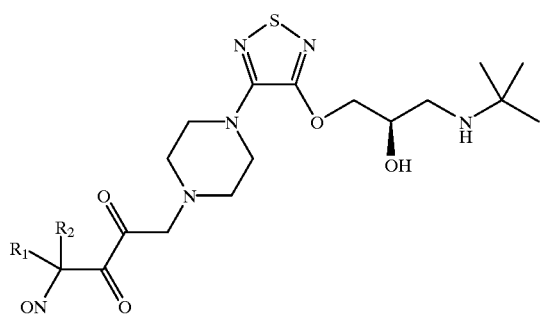

(20)
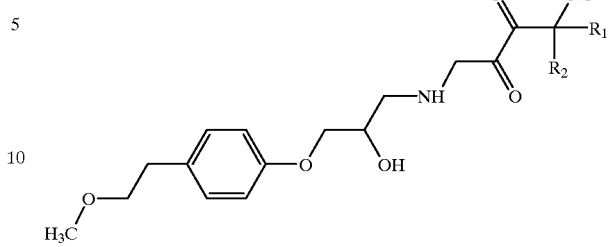

(21)
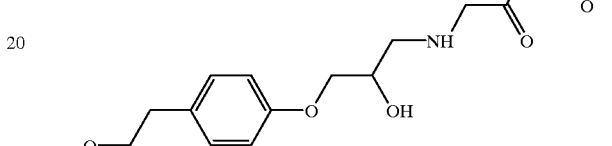

(22)
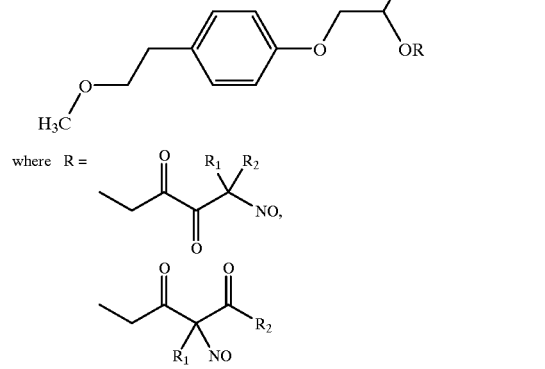

In compounds (14), (15), (16), (17), (18) and (19), $R_1$ and $R_2$ are selected from the group consisting of $C_1$–$C_6$ alkyl and $C_6$–$C_{20}$ aryl and substituted derivatives thereof e.g., substituted with amino, hydroxy and/or carboxy and/or which are sulfated and/or phosphorylated.

The antihypertensive metoprolol has the formula:

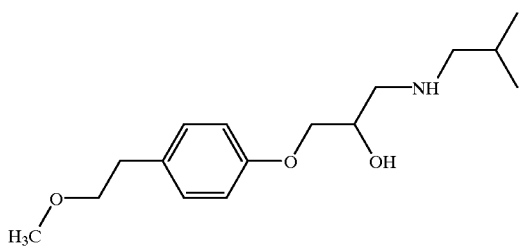

C-Nitroso compounds of the invention derived from metoprolol include, for example:

(23)
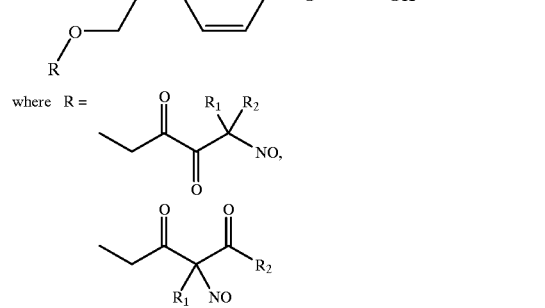

In compounds (20), (21), (22) and (23), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antihypertensive pindalol has the formula:

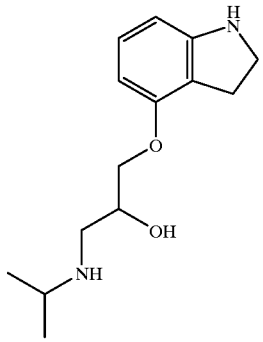

C-Nitroso compounds of the invention derived from pindalol include, for example:

(24)

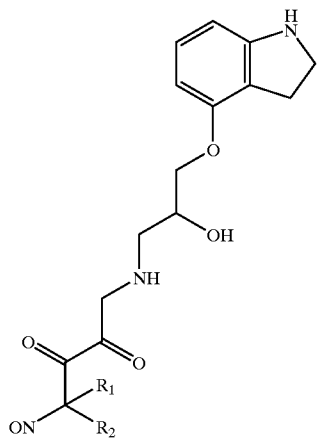

where R =

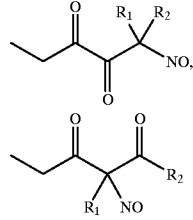

(25)

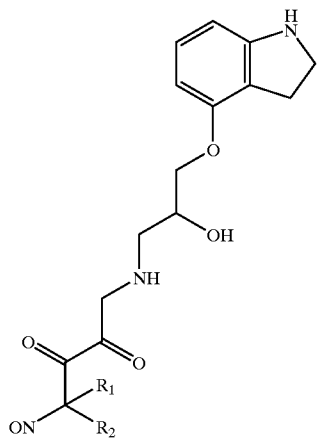

(26)

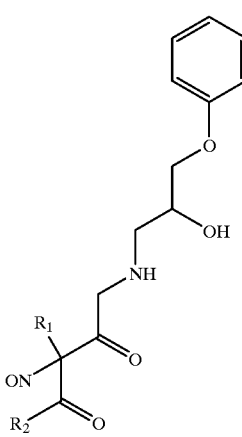

(27)

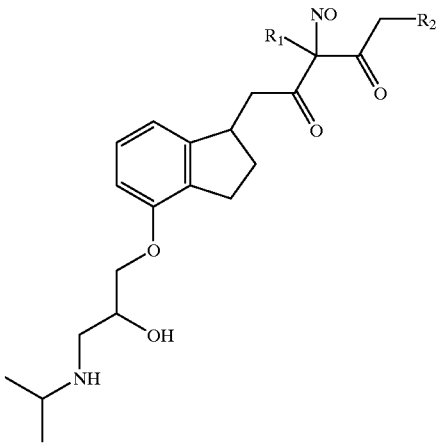

(28)

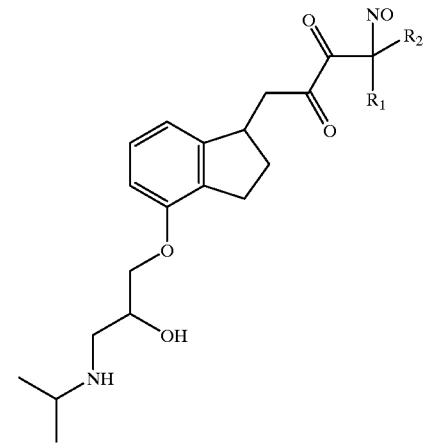

Are (27) and (28) correct—note no N in ring?

In (24), (25), (26), (27) and (28), $R_1$ and $R_2$ are selected from the group consisting of $C_1$–$C_6$ alkyl and $C_1$–$C_6$ aryl and substituted derivatives thereof, e.g., substituted with amino, hydroxyl and/or carboxy and/or which are sulfated and/or phosphorylated.

The antihypertensive labetalol has the formula:

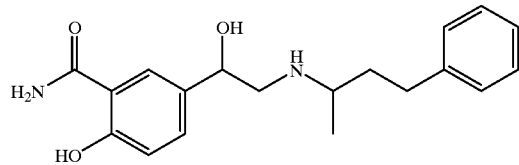

C-Nitroso compounds of the invention derived from labetalol include, for example:

(29)

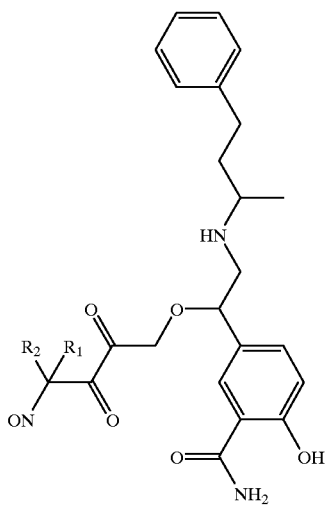

(30)

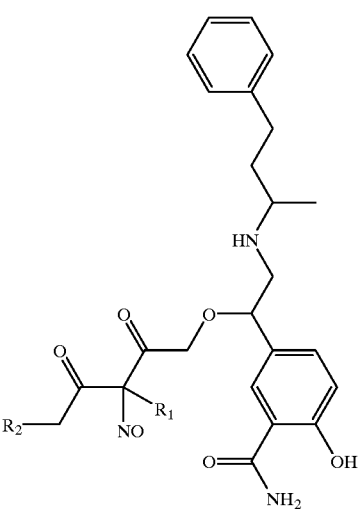

(31)

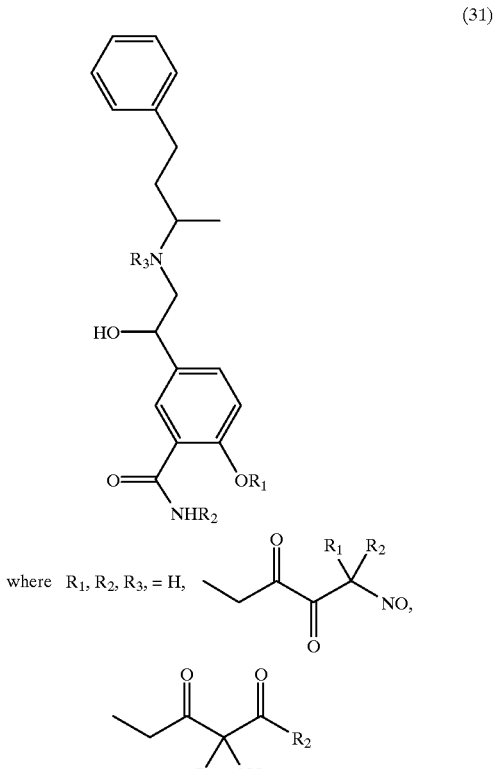

where $R_1, R_2, R_3, = H,$ 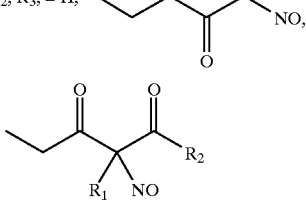

(32)

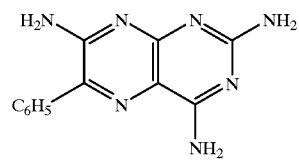

where R = [structures as shown]

In (29), (30), (31) and (32), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The diuretic triamterene has the formula:

[triamterene structure]

C-Nitroso compounds of the invention derived from triampterene include, for example:

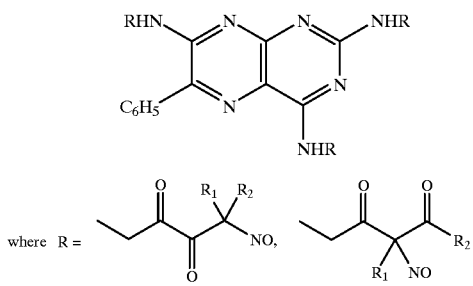

(33)

where R = [two structures shown]

In (33), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The diuretic furosemide has the formula:

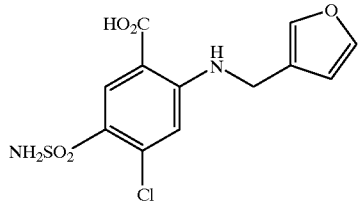

C-Nitroso compounds of the invention derived from furosemide are uniquely useful in treating heart failure in combining diuretic and vasodilator functions and include, for example:

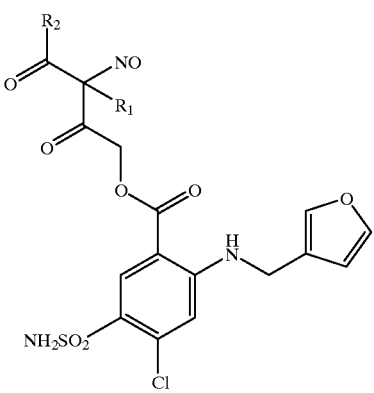

(34)

(35)

(36)

(37)

In (34), (35), (36) and (37), $R_1$ and $R_2$ are selected from the group consisting of $C_1$–$C_6$ alkyl and $C_6$–$C_{20}$ aryl and substituted derivatives thereof e.g., substituted with amino, hydroxyl and/or carboxy and/or which are sulfated and/or phosphorylated.

The ACE inhibitor enalapril has the formula:

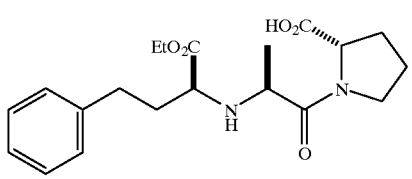

C-Nitroso compounds of the invention herein derived from enalapril have improved antianginal effect when used to lower blood pressure and improved antiplatelet activity and include, for example:

(38)
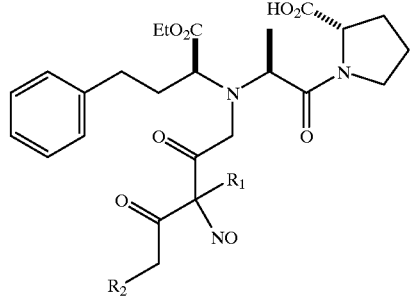

(39)
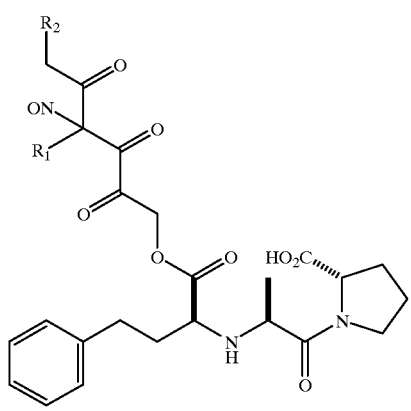

(40)
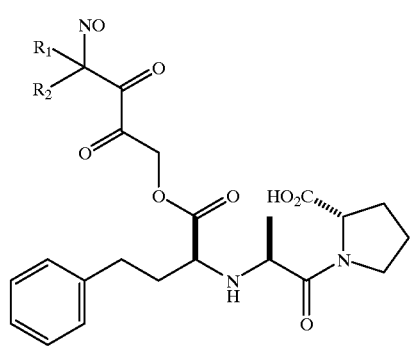

(41)
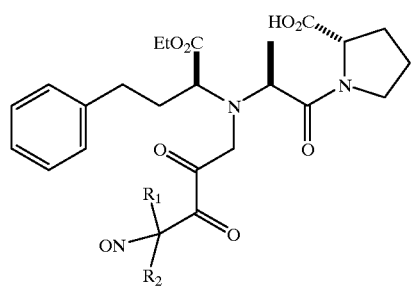

In (38), (39), (40) and (41), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The ACE inhibitor rampiril has the formula:

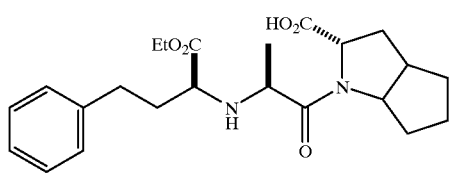

C-Nitroso compounds of the invention herein derived from rampiril include, for example:

(42)
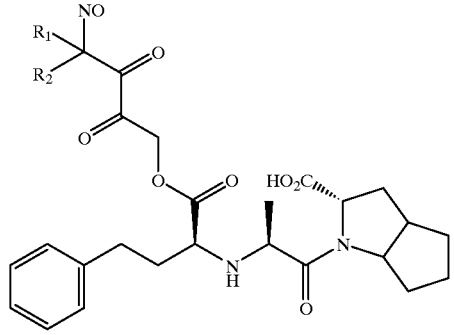

(43)
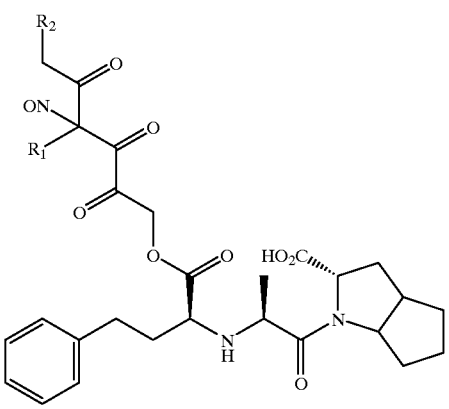

(44)
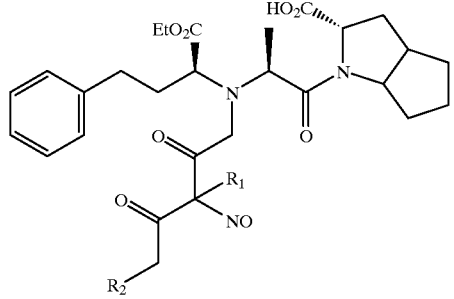

(45)

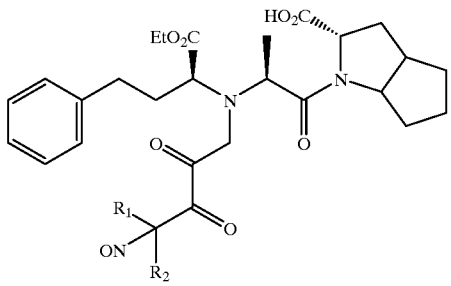

(47)

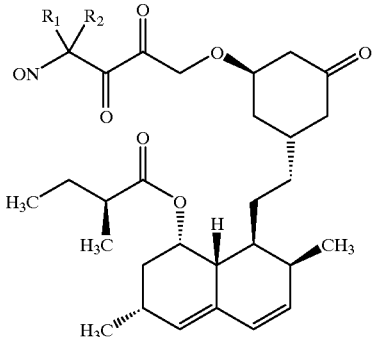

In (42), (43), (44) and (45), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antihypercholesterolemic/antihyperlipoproteinemic lovastatin has the formula:

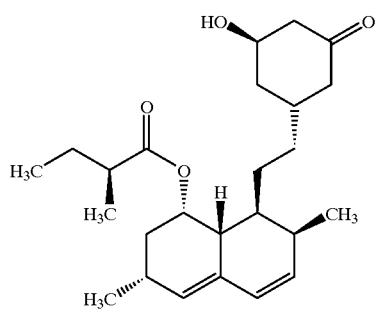

C-Nitroso compounds of the invention herein derived from lovastatin include, for example:

(46)

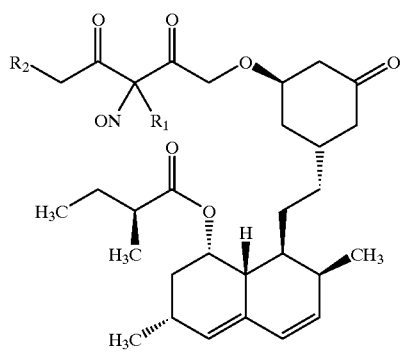

(48)

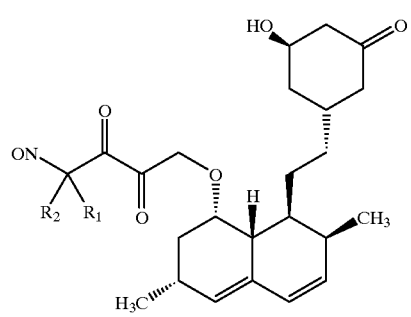

(49)

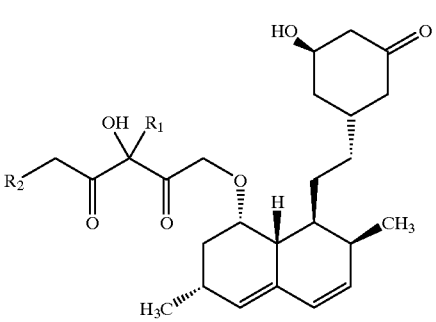

In (46), (47), (48) and (49), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antihypercholesterolemic/antihyperlipoproteinemic pravastatin has the formula:

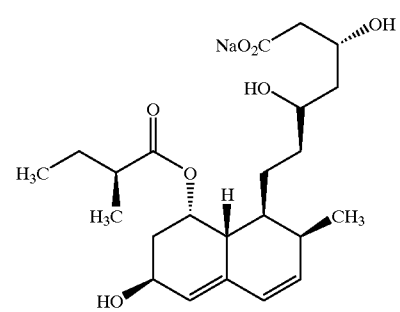

C-Nitroso compounds of the invention herein derived from pravastatin include, for example:

(50)

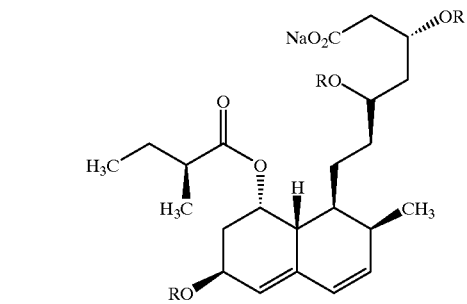

where R = H,

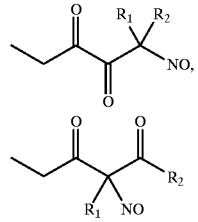

(51)

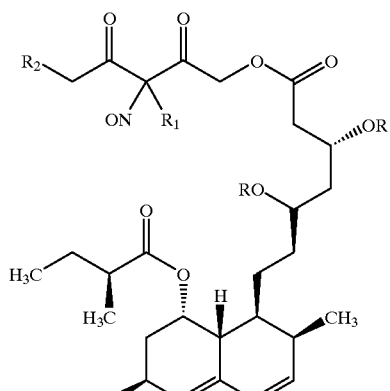

where R = H,

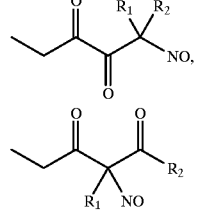

(52)

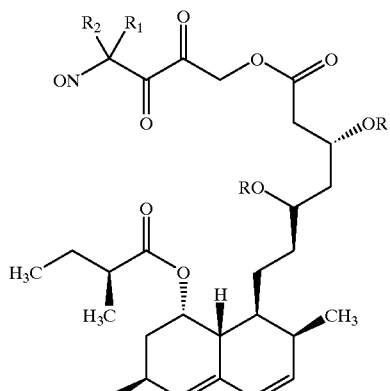

-continued where R = H,

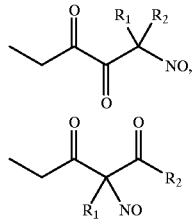

(53)

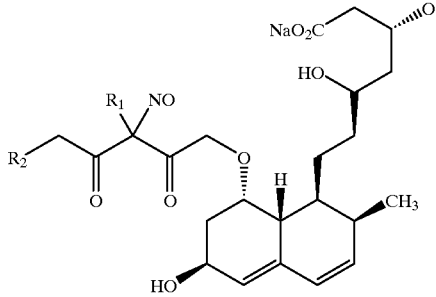

(54)

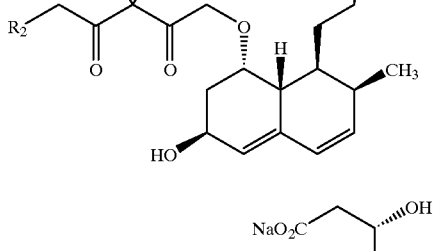

In (50), (51), (52), (53) and (54), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antihypercholesterolemic/antihyperlipoproteinemic gemfibrozil has the formula:

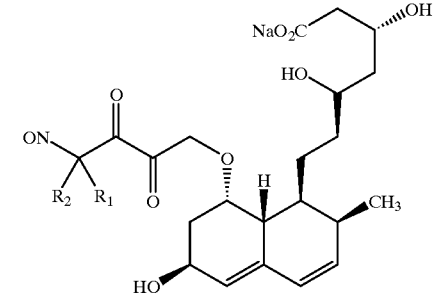

C-Nitroso compounds of the invention herein derived from gemfibrozil include, for example:

(55)

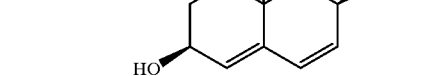

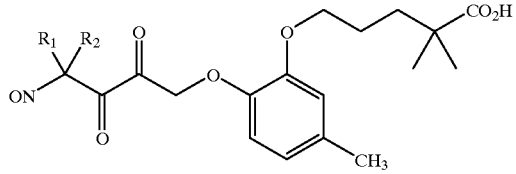
(56)

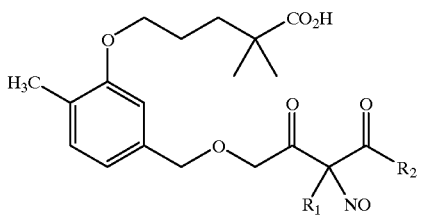
(57)

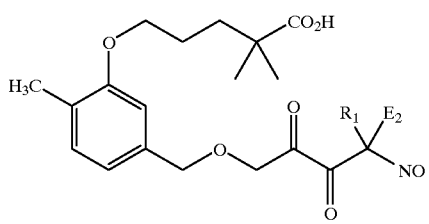
(58)

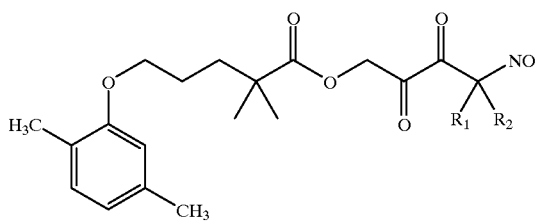
(59)

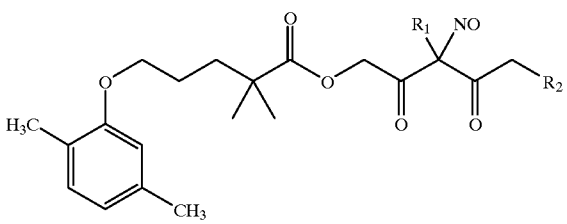
(60)

In (55), (56), (57), (58), (59) and (60), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antihypercholesterolemic/antihyperlipoproteinemic clofibrate has the formula:

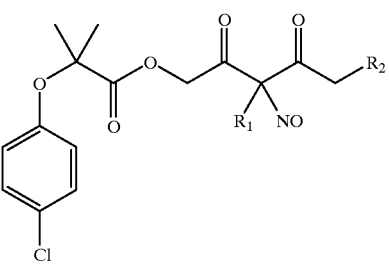

C-Nitroso compounds of the invention herein derived from clofibrate include, for example:

(61)

(62)

In (61 and (62), $R_1$ and $R_2$ are selected from the group consisting of $C_1$–$C_6$ alkyl and $C_6$–$C_{20}$ aryl and substituted derivatives thereof e.g., substituted with amino, hydroxyl and/or carboxy and/or which are sulfated and/or phosphorylated.

The calcium channel blocker nifedipine has the formula:

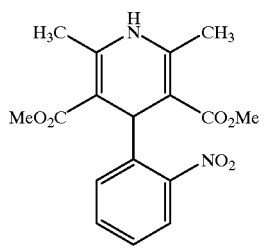

C-Nitroso compounds derived from nifedipine include, for example:

(63)

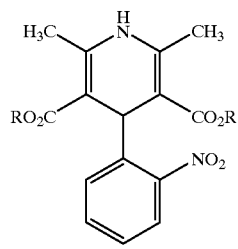

where R =Me,

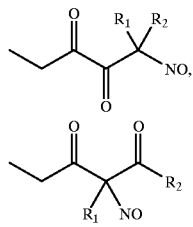

(64)

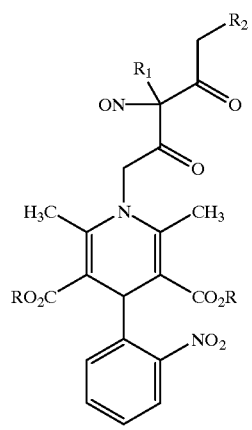

where R is as in (63)

(65)

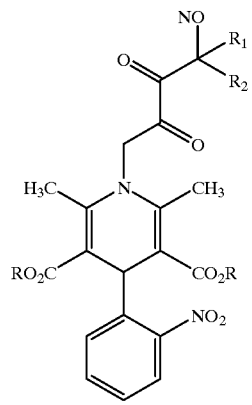

-continued where R is as in (63)

In (63), (64) and (65), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The calcium channel blocker amlodipine has the formula:

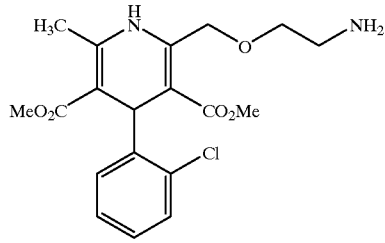

C-Nitroso compounds of the invention herein derived from amlodipine include, for example:

(66)

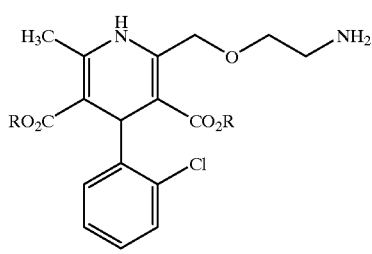

where R = Me,

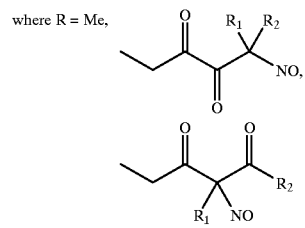

(67)

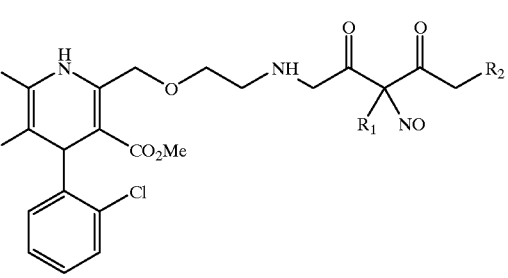

(68)
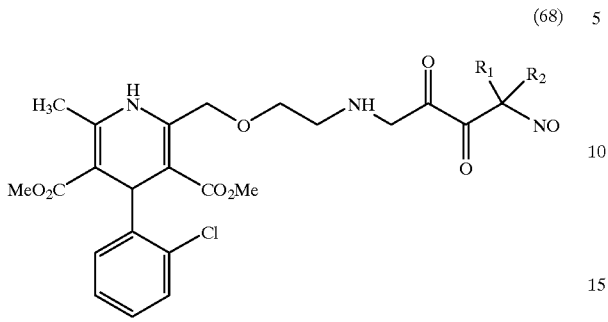

(69)
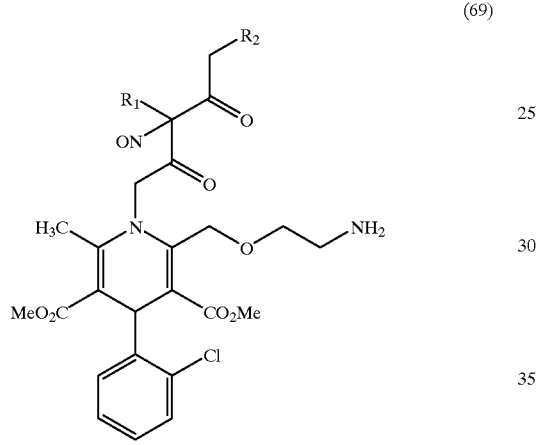

(70)
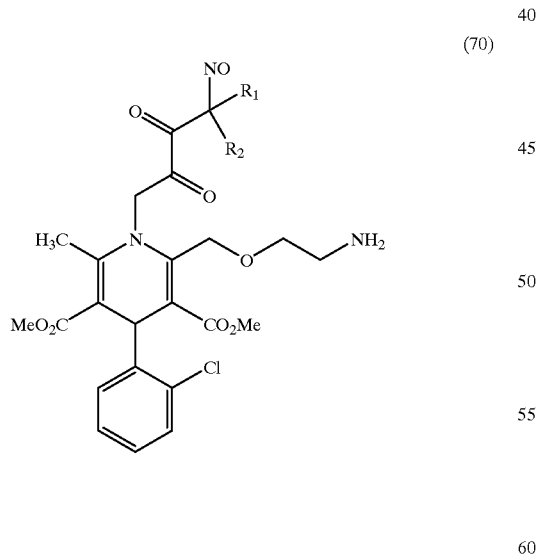

In (66), (67), (68), (69) and (70), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The calcium channel blocker diltiazem has the formula:

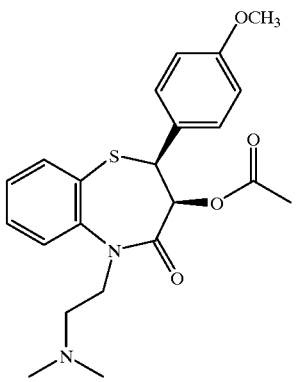

C-Nitroso compounds of the invention herein derived from diltiazem include, for example:

(71)
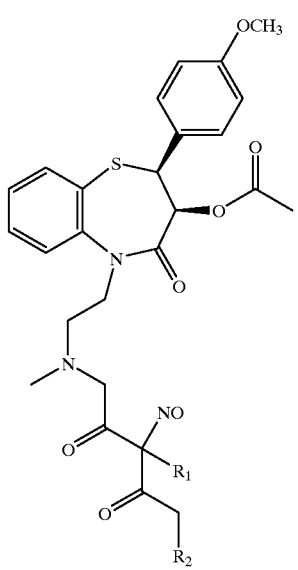

(72)
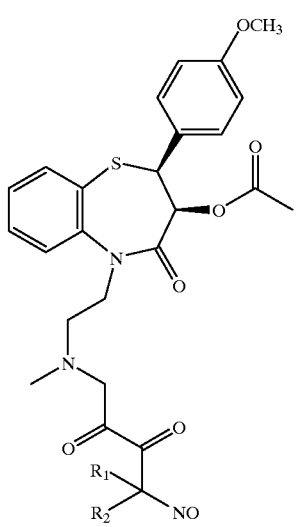

(73)
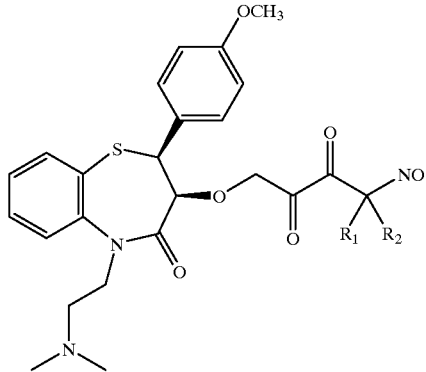

(74)
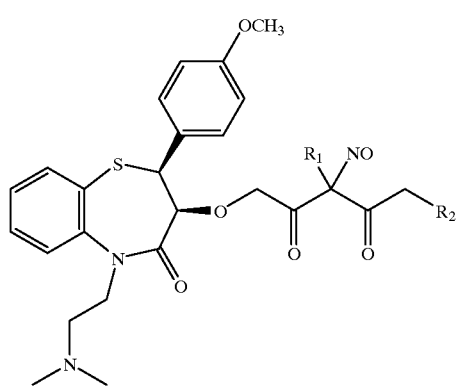

(75)
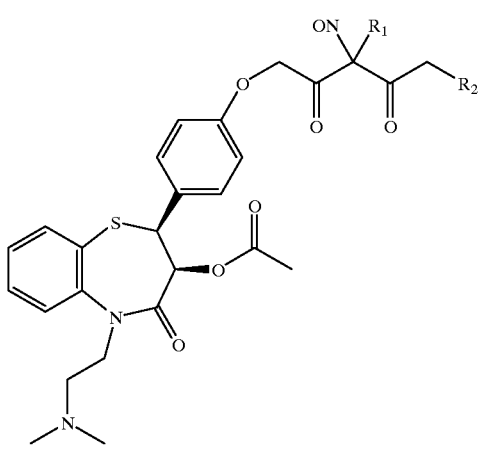

(76)
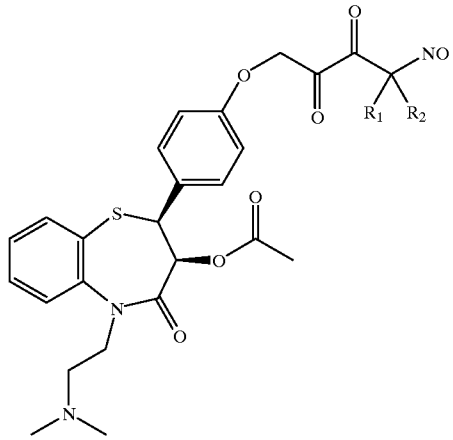

In (71), (72), (73), (74), (75) and (76), $R_1$ and $R_2$ are selected from the group consisting of $C_1$–$C_6$ alkyl and $C_6$–$C_{20}$ aryl and substituted derivatives thereof e.g., substituted with amino, hydroxyl and/or carboxy and/or which are sulfated and/or phosphorylated.

The calcium channel blocker verapamil has the formula:

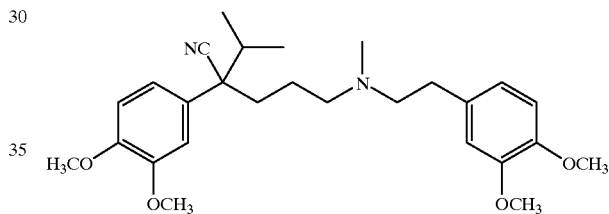

C-Nitroso compounds of the invention herein derived from verapamil include, for example:

(77)
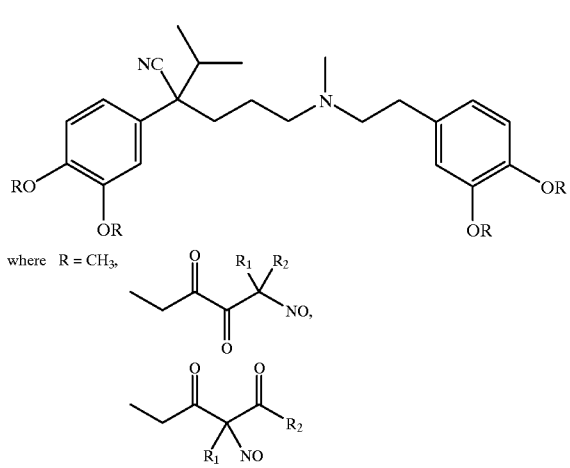

-continued

(78)
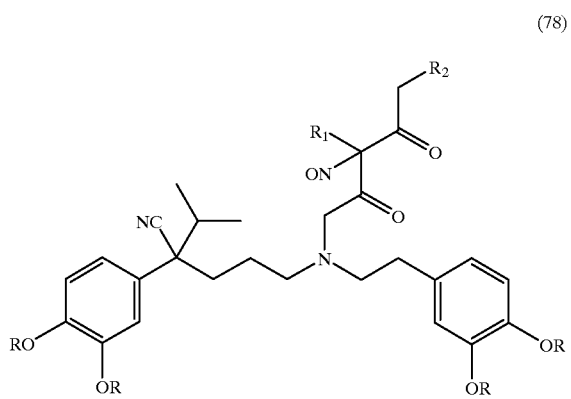

where R is the same as for (77)

(79)
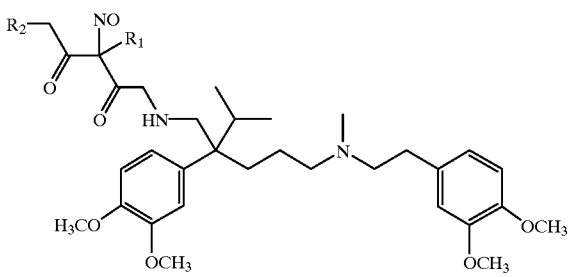

(80)
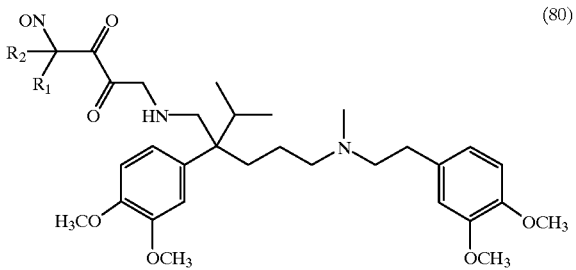

(81)
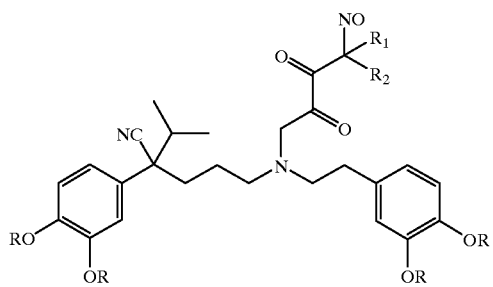

where R is the same as in (77)

In (77), (78), (79), (80) and (81), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antacid cimetidine has the formula:

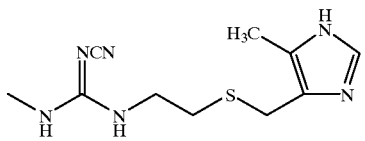

C-Nitroso compounds of the invention herein derived from cimetidine include, for example:

(82)
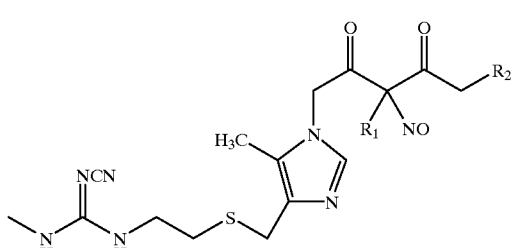

(83)
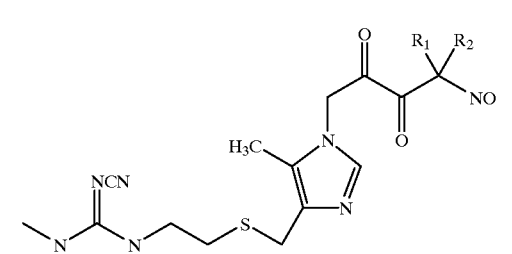

In (82 and (83), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antacid ranitidine has the formula:

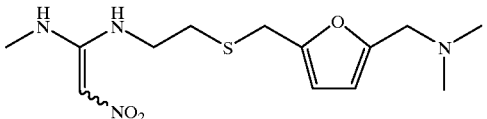

C-Nitroso compounds of the invention herein derived from ranitidine include, for example:

(84)
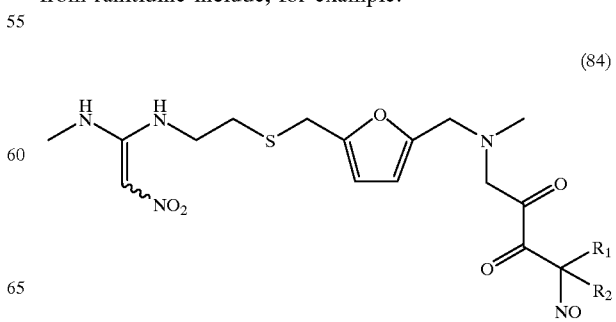

(85)

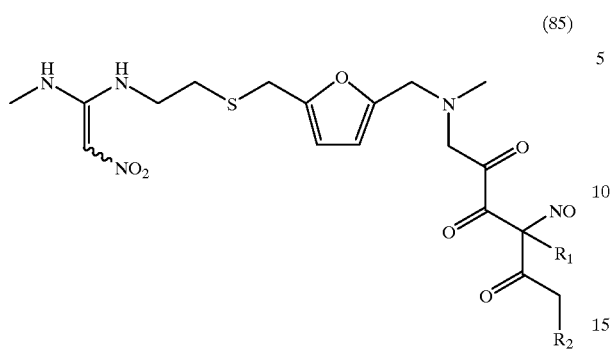

In (84) and (85), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The bronchodilator albuterol has the formula:

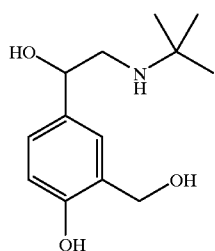

C-Nitroso compounds of the invention herein derived from albuterol include, for example:

(86)

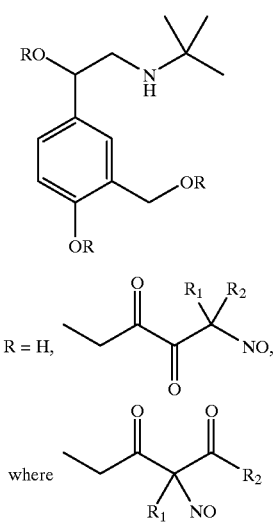

(87)

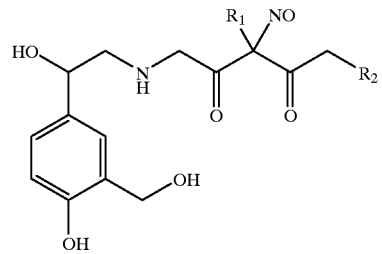

(88)

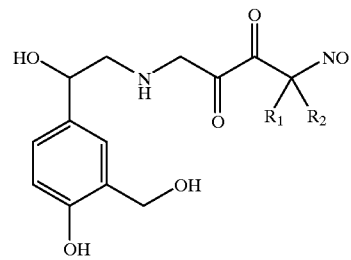

In (86), (87) and (88), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The bronchodilator ipratropium bromide has the formula:

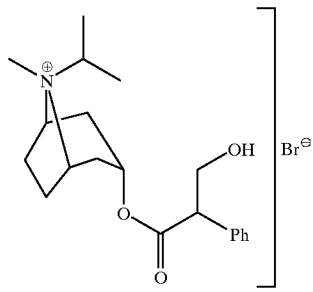

C-Nitroso compounds of the invention herein derived from ipratropium bromide include, for example:

(89)

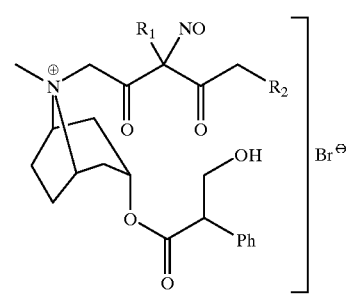

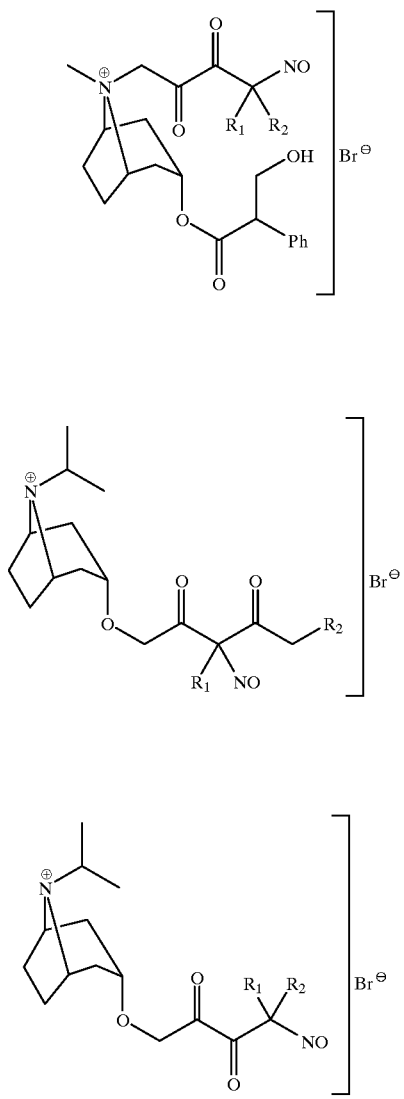

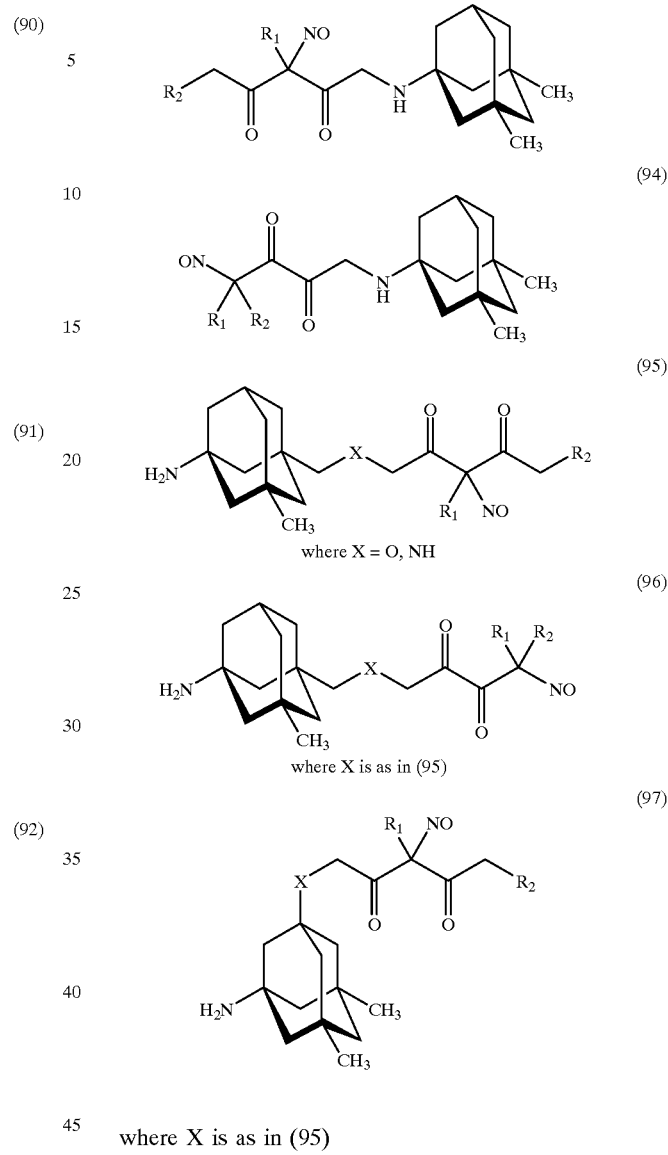

where X is as in (95)

In (93), (94), (95), (96) and (97), $R_1$ and $R_2$ are selected from the group consisting of $C_1$–$C_6$ alkyl and $C_6$–$C_{20}$ aryl and substituted derivatives thereof e.g., substituted with amino, hydroxyl and/or carboxy and/or which are sulfated and/or phosphorylated.

C-Nitroso derivatives of antiproliferative agents are especially useful, as the NO group has antiproliferative effect and increases that of the agent before NO derivatization.

The antiproliferative/tubulin binding agent 10-deacetylbaccatin HI has the formula:

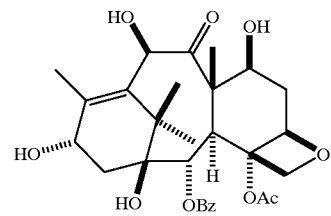

In (89), (90), (91), and (92), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The NMDA antagonist/skeletal muscle relaxant memantine has the formula:

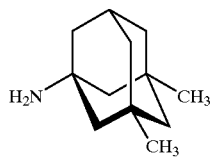

C-Nitroso compounds of the invention herein derived from memantine include, for example:

C-Nitroso compounds of the invention herein that are derivatives of 10-deacetyl-baccatin III include, for example:

(98)

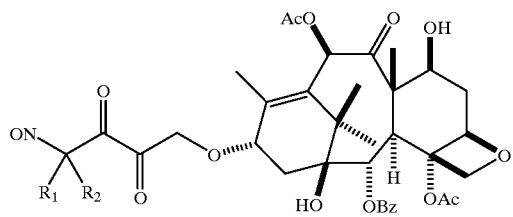

(99)

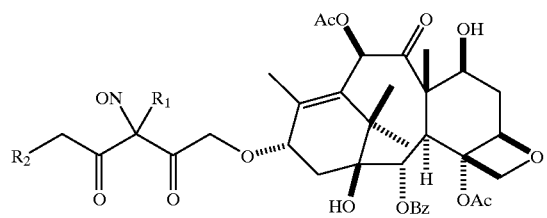

In (98) and (99), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The antiproliferative/tubulin binding agent taxol has the formula:

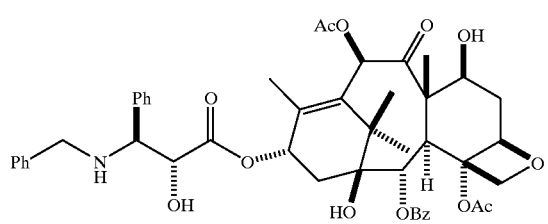

C-Nitroso compounds of the invention herein derived from taxol include, for example:

(100)

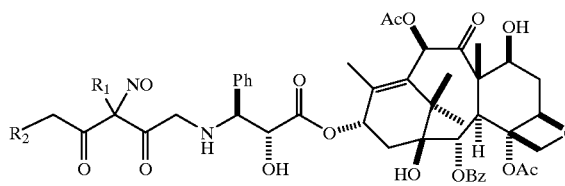

(101)

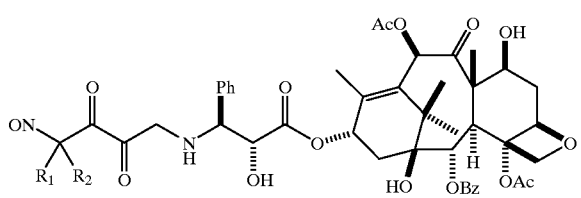

In (100) and (101), $R_1$ and $R_2$ are selected from the group consisting of $C_1$–$C_6$ alkyl and $C_6$–$C_{20}$ aryl and substituted derivatives thereof e.g., substituted with amino, hydroxyl and/or carboxy and/or which are sulfated and/or phosphorylated.

The antitubercular PA-824 has the formula:

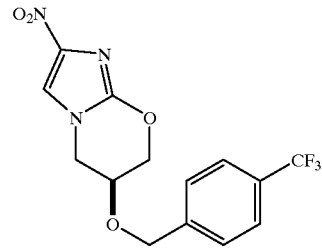

C-Nitroso compounds of the invention herein derived from PA-824 include, for example:

(102)

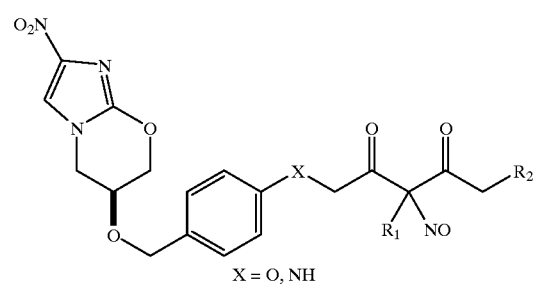

X = O, NH (103)

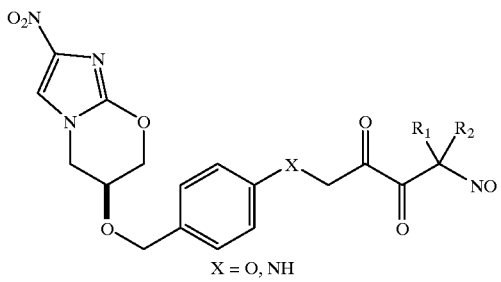

X = O, NH

In (102) and (103), $R_1$ and $R_2$ are selected from the group consisting of $C_1$–$C_6$ alkyl and $C_6$–$C_{20}$ aryl and substituted derivatives thereof e.g., substituted with amino, hydroxyl and/or carboxy and/or which are sulfated and/or phosphorylated.

The CETP inhibitor JTT-705 (Okamoto et al., Nature 406, 203 (2000)) has the formula:

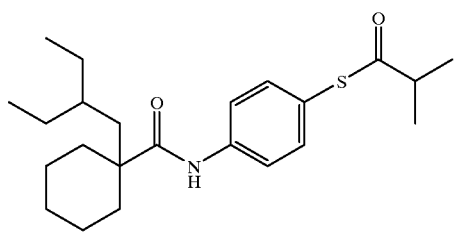

C-Nitroso compounds of the invention herein derived from JTT-705 include, for example:

(104)
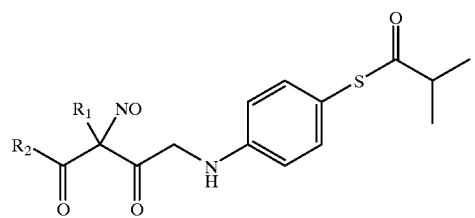

(105)
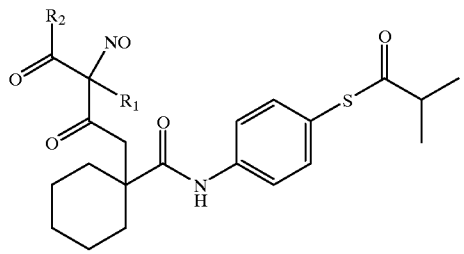

(106)
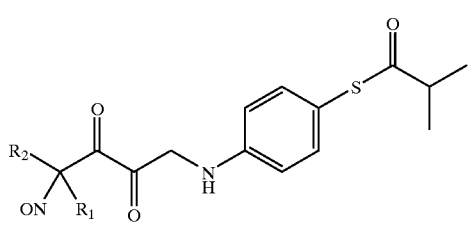

(107)
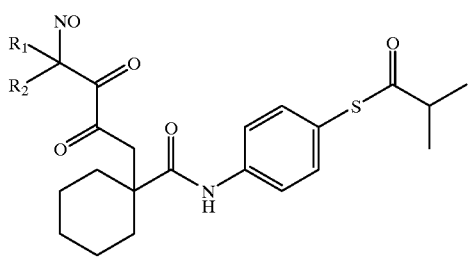

(108)
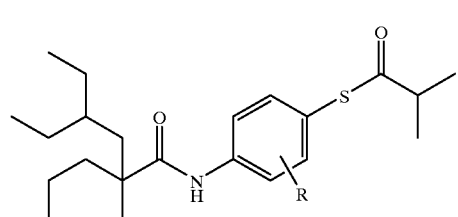

R = 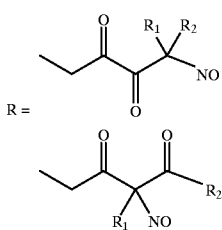

In (104), (105), (106), (107) and (108), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

C-Nitroso compounds derived from SOD mimetics include, for example:

(109)
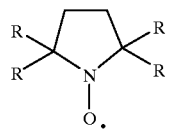

where R is H, $C_1$–$C_6$ alkyl, $C_6$–$C_{20}$ aryl,

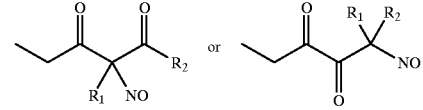 or 

(110)
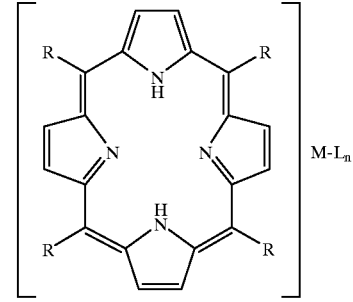

where M is, for example, manganese, iron or cobalt, L is halide, n ranges from 0 to 4 depending on the valence of M, and R is as in (109).

In (109) and (110), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The xanthine oxidase inhibitor allopurinol has the formula:

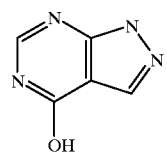

C-Nitroso compounds derived from allopurinol include, for example:

(111)
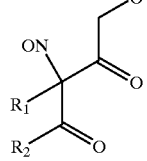
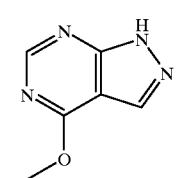

(112)
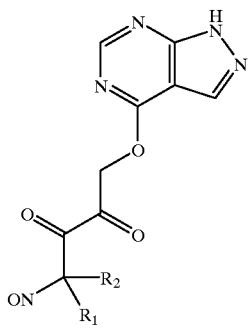

(115)
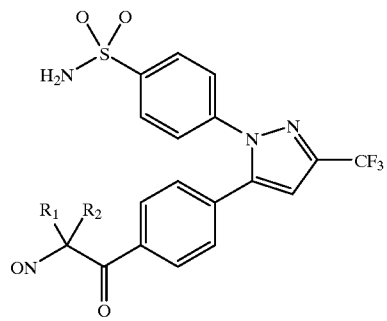

(113)
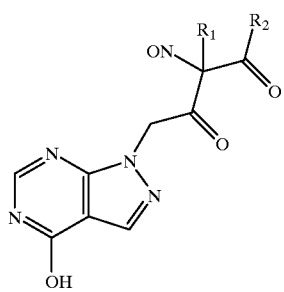

(116)
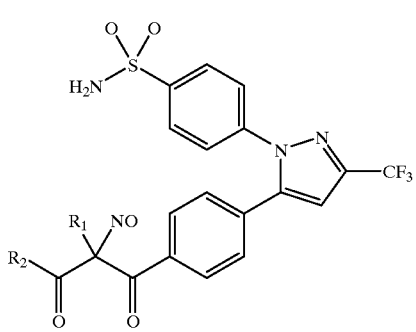

(114)
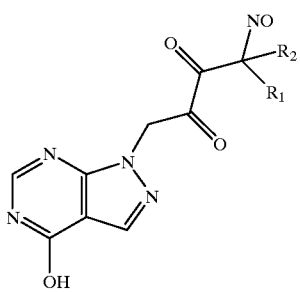

(117)
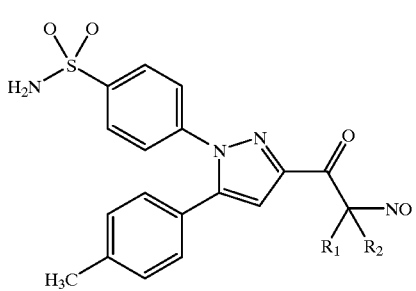

In (111), (112), (113) and (114), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The COX-2 inhibitor Celebrex has the formula:

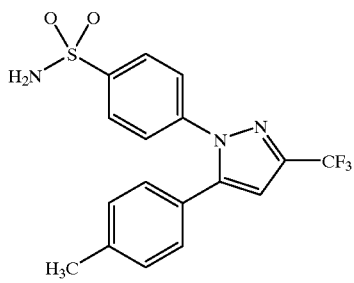

C-Nitroso compounds derived from Celebrex include, for example:

(118)

In (115), (116), (117) and (118), $R_1$ and $R_2$ are selected from the group consisting of $C_1$–$C_6$ alkyl and $C_6$–$C_{20}$ aryl and substituted derivatives thereof e.g., substituted with amino, hydroxyl and/or carboxy and/or which are sulfated and/or phosphorylated.

The COX-2 inhibitor indomethacin has the formula:

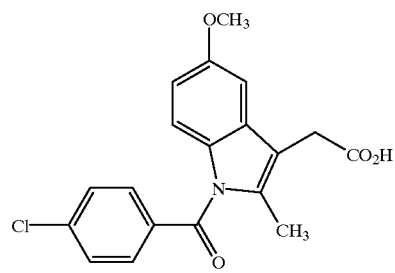

C-Nitroso compounds derived from indomethacin include, for example:

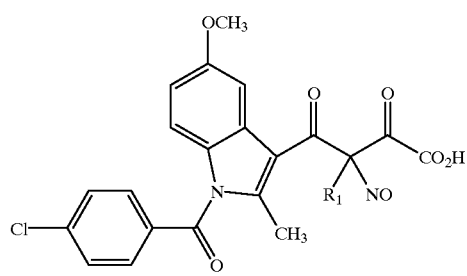
(119)

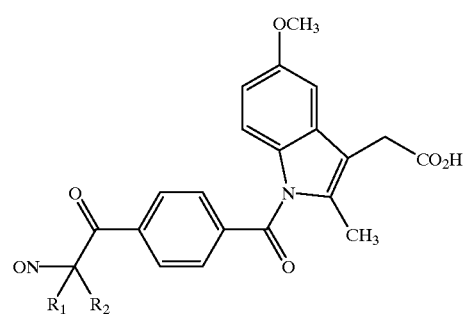
(120)

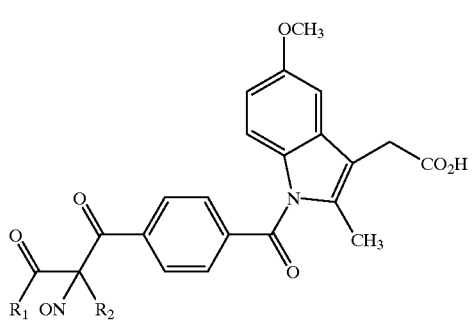
(121)

In (119), (120) and (121), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated.

The COX-2 inhibitor L-745,337 has the formula:

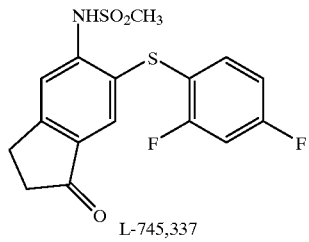
L-745,337

C-Nitroso compounds derived from L-745,337 include, for example:

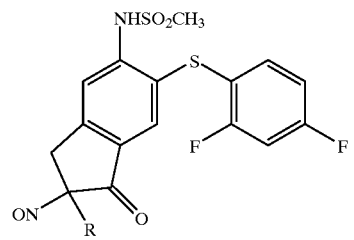
(122)

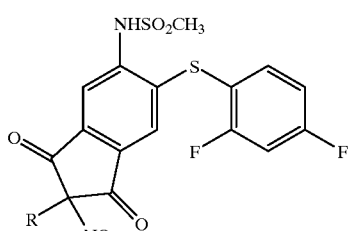
(123)

(124)

In (122), (123) and (124):

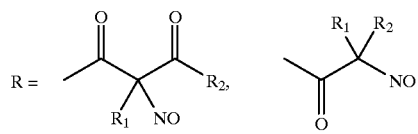

and $R_1$ and $R_2$ are selected from the group consisting of $C_1$–$C_6$ alkyl $C_6$–$C_{20}$ aryl and substituted derivatives thereof, e.g., amino, hydroxyl and/or carboxy and/or which are sulfated and/or phosphorylated.

The COX-2 inhibitor etudolac has the formula:

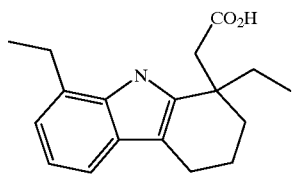

C-Nitroso compounds derived from etudolac include, for example:

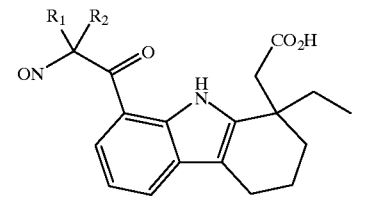
(125)

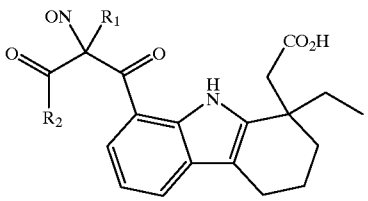
(126)

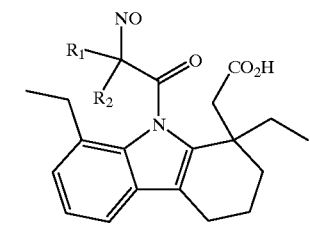
(127)

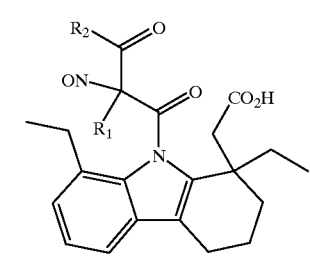
(128)

In (125), (126), (127) and (128), $R_1$ and $R_2$ are selected from the group consisting of $C_1$–$C_6$ alkyl, $C_6$–$C_{20}$ aryl and substituted derivatives thereof, e.g., substituted with amino, hydroxyl and/or carboxy and/or which are sulfated and/or phosphorylated.

In all cases where $R_1$, $R_2$, $R_3$, $R_4$ or $R_5$ are defined above where H is not one of the named groups, $R_1$, $R_2$, $R_3$, $R_4$ and $R_5$ can also be H, provided that the NO is attached to a tertiary carbon, i.e., so that defining $R_1$, $R_2$, $R_3$, $R_4$ and/or $R_5$ as H does not make NO attached to a carbon which is not a tertiary carbon.

The compounds (1)–(128) are meant to be exemplary and as one skilled in the art would understand, in many cases the chain on which the NO is substituted can also be in a different location from the one depicted.

In many of the exemplified compounds, the nitric oxide bearing fragment is linked through an ether or amino linkage. The ether linkage has the advantage of stability in vivo. Alternatively, in some instances it can be advantageous to link the NO-bearing fragment through an ester linkage.

Examples of C-nitroso compounds of the invention herein where NO-bearing fragment is linked through an ester linkage are set forth below:

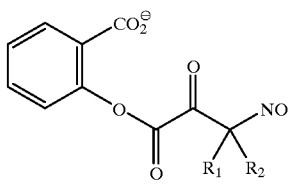
(129)

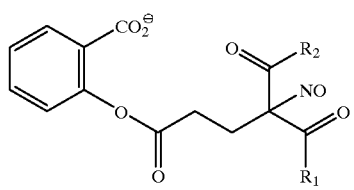
(130)

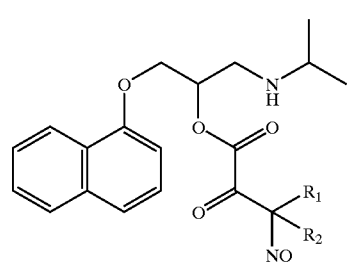
(131)

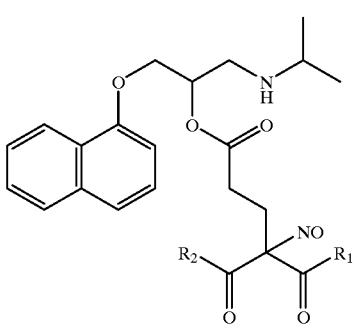
(132)

In (129), (130), (131) and (132), $R_1$ and $R_2$ are selected from the group consisting of $C_1$–$C_6$ alkyl and $C_6$–$C_{20}$ aryl and substituted derivatives thereof, e.g., substituted with amino, hydroxyl and/or carboxy and/or which are sulfated and/or phosphorylated, or can be H, provided that defining $R_1$ and $R_2$ as H does not make NO attached to a carbon which is not a tertiary carbon. The compounds (129), (130), (131) and (132) are meant to be exemplary, and knowing the above, one skilled in the art, could conceive of many other C-nitroso compounds of the invention herein where NO-bearing fragment is linked through an ester linkage.

An example of a Compound (129) is:

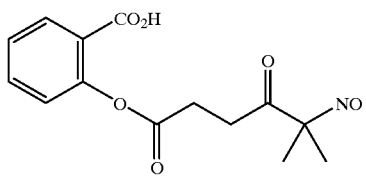
(129a)

An example of a Compound (130) is:

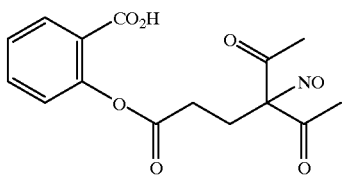
(130a)

Both the compounds (129a) and (130a) are obtained by nitrosylation of a carbon atom having a pKa less than about 10.

We turn now to the synthesis of the C-nitroso compounds of the first embodiment herein.

Several methods applicable to synthesizing C-nitroso compounds are disclosed in Boyer, J. H, "Methods of Formation of the Nitroso Group and its Reactions" in The Chemistry of the Nitro and Nitroso Groups, Part 1, Feuer, H., Editor, John Wiley & Sons, New York (1969) at pages 215–299 and in Touster, O. in Organic Reactions, Vol. 7, John Wiley & Sons, New York (1955) at pages 327–377 which are incorporated herein by reference.

In a method which is applicable to nitrosylation of carbon acids with pKa's less than about 15, the carbon acids can be directly nitrosylated with sodium nitrite and an acid such as glacial acetic acid after the method of Sklyar, Yu. E., et al., Khimiya Geterotsiklicheskikh Soedinenii, 5, 70–73 (1969). This method is useful for preparing the subgenus of compounds herein which are obtained by nitrosylation of a carbon acid having a pKa less than about 10.

In a method which is applicable to nitrosylating carbon acids with pKa's between about 15 and 30, nitrosylation is carried out by formation of the enolate and trapping the enolate by a nitrosonium equivalent. The enolate can be trapped directly or isolated as the silyl enol ether or an equivalent. This method is useful for preparing the subgenus of compounds herein obtained by nitrosylation of a carbon acid having a pKa ranging from about 15 to about 20. It is the method used in Example I hereinafter for preparing dimeric 2-[4'-(α-nitroso)isobutyrylphenyl]propionic acid.

In a method useful for synthesizing C-nitroso compounds regardless of the acidity, the carbon acid is converted to the corresponding hydroxyl amine which is oxidized, for example, using silver carbonate on Celite.

In the case of unstable C-nitroso compounds, it can be desirable to introduce or unmask the C-nitroso fragment only in the final step of the synthesis, or at least as late in the synthesis as possible. In one such route, the synthesis of the C-nitroso drug will first incorporate an appropriate fragment and nitrosylation is carried out only after synthesis is complete. An example of this route is set forth below:

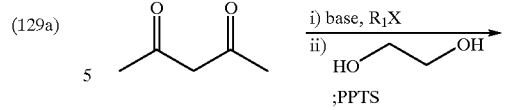

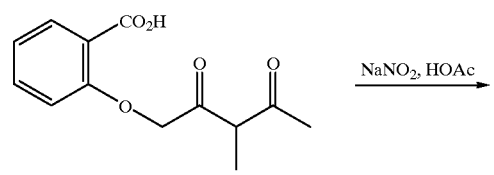

In the above reaction scheme, R, can be selected from the group consisting of $C_1$–$C_6$ alkyl and $C_6$–$C_{20}$ aryl and substituted derivatives thereof (as defined for $R_1$ and $R_2$ above), and X is chlorine or bromine and PPTS is pyridinium paratoluene sulfonic acid and "pyr" is pyridine. This route is especially suitable for the preparation of compounds derived from parent carbon acids with especially low pKa values, typically less than 15 and preferably less than 10. For compounds derived from parent carbon acids with higher pKa values, it is preferable to carry the C-nitroso moiety masked as the bis-protected hydroxylamine; the C-nitroso functionality is unmasked, for example, late in the synthesis, following attachment to a conventional drug, by mild oxidation with, for example, silver carbonate on Celite; an example of this mode of synthesis is set forth below:

51

-continued

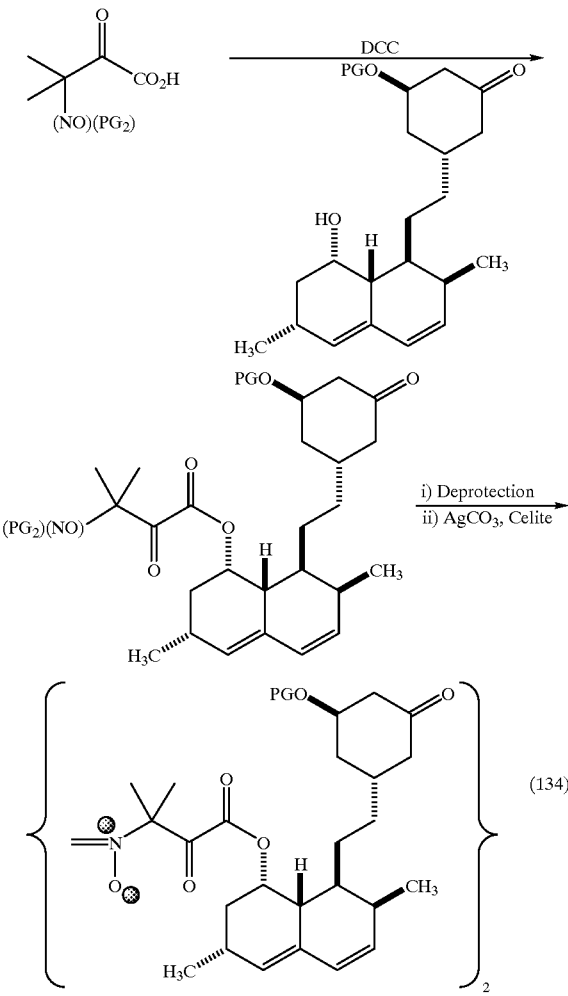

(134)

In this reaction, LDA means lithium diisopropyl amide, TMSE means trimethylsilylethyl, R is TMSE, PG is a protecting group, and DCC is dicyclohexylcarbodiimide.

Derivatized compounds can be prepared utilizing as nitrosylating agent a bromomethylketone derivative of either 3-nitroso-2,4-pentane dione or 4-nitroso-2,3-butadione.

Substituted 3-nitroso-2,4-pentadiones can be prepared by the following reaction scheme:

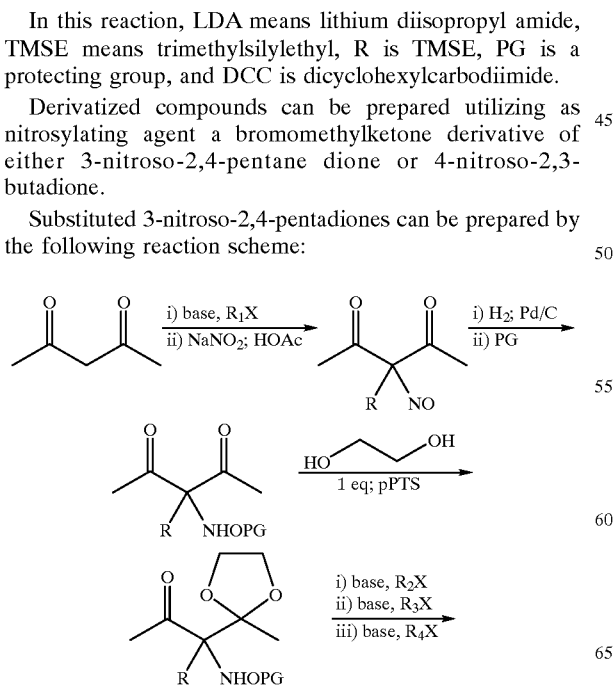

52

-continued

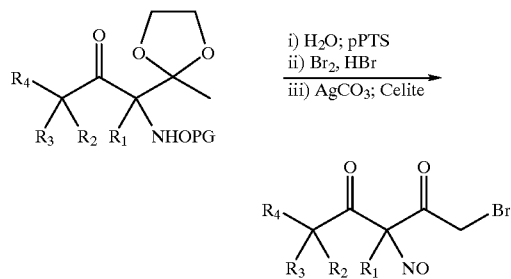

In the above reaction, scheme "PG" stands for protecting group and "pPTS" stands for pyridinium paratoluene sulfonic acid, $R_1$, $R_2$, $R_3$ and $R_4$ are the same or different and can be the same as $R_1$ is defined for reaction schemes above, and X is chlorine or bromine. The preparation is briefly described as follows: A group is introduced by nucleophilic substitution at the most acidic position in standard fashion. Introduction of this group prevents formation of the oxime following nitrosylation. The precise identity of the group is chosen to control the reactivity of the C-nitroso derivative. Electrophilic nitrosylation with nitrosonium is followed by reduction to the hydroxylamine and protection as the bisacyl derivative, as described in "Bis-protected hydroxylamines as reagents in organic synthesis. A review:" in Romine, J. L., Org. Prep. Proced. Int. 28, 249–288 (1996). Differentiation of the dione by monoprotection as the ketal is followed by introduction of one, two or three groups by nucleophilic substitution in the standard way.

Deprotection of the ketal and the hydroxyl amine is followed by mild oxidation to the C-nitroso compound with, for example, silver (1) salts immobilized on Celite. Finally, conversion to the bromomethyl ketone with bromine and hydrobromic acid provides the derivatizing agent.

Substituted 4-nitroso-2,3-butadiones can be prepared according to the following reaction scheme:

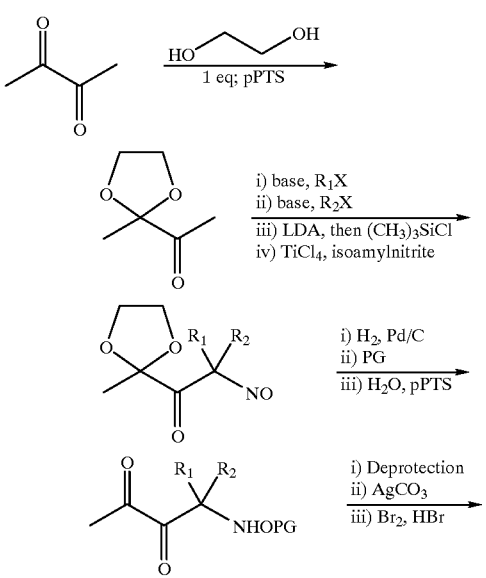

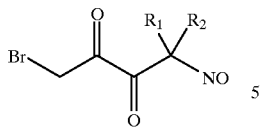

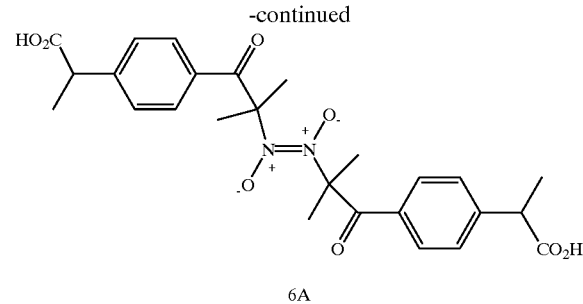

6A

In the above reaction scheme, "pPTS" is pyridimium para-toluene sulfonic acid, "LDA" is lithium diisopropyl amide and "PG" means protecting group $R_1$ and $R_2$ can be the same or different and can be the same as for the reaction schemes set forth above, and X is chlorine or bromine. The preparation is briefly described as follows: The dione of 2,3-butadione is differentiated as the monoketal and is then substituted by nucleophilic substitution in the standard fashion. Nitrosylation through the silyl enol ether, followed by protection of the C-nitroso group as the diacylated hydroxylamine precedes deprotection of the ketal, regeneration of the C-nitroso functionality and bromination to the reactive α-bromoketone.

In the synthesis of compounds of the first embodiment herein, the carbon acid pKa of the starting material can be adjusted down by the provision therein of an electron withdrawing group and the carbon acid pKa can be adjusted up by the provision therein of an electron releasing group.

For example, an acidic center can be introduced, e.g., formation of a ketone group from the carbon adjacent the carbon to be nitrosylated to increase the acidity and provide lower carbon acid pKa starting material. This approach was used in the synthesis of dimeric 2-[4'-(α-nitroso)isobutyrylphenyl]propionic acid from ibuprofen set forth in Example I below. In the synthesis of Example I, ibuprofen (carbon acid pKa of approximately 50–55) was converted to 2-(4'-isobutyrylphenyl)propionic acid (carbon acid pKa of about 20) by this approach and the latter was converted to the final product by the method of nitrosylating carbon acids with pKa's between about 15 and 30 described above. The reaction scheme used in Example I to convert ibuprofen to dimeric 2-[4'-(α-nitroso)isobutyrylphenyl]propionic acid is set forth below where 1A is ibuprofen, 4A is 2-(4'-isobutyrylphenyl)propionic acid and 6A is the dimeric product.

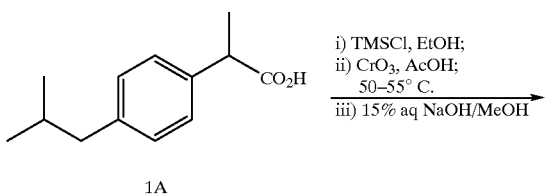

1A i) TMSCl, EtOH;
ii) CrO₃, AcOH;
    50–55° C.
iii) 15% aq NaOH/MeOH

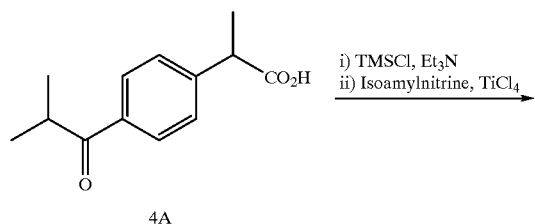

4A i) TMSCl, Et₃N
ii) Isoamylnitrine, TiCl₄

In the above reaction scheme, "TMSCl" stands for chlorotrimethylsilane.

In summary, there are fundamentally at least two different ways of making compounds herein. One of these is to modify the parent drug to introduce of the first embodiment herein functionality (ketone or dione) that allows C-nitrosylation. It is by this method that the nitrosoketoibuprofen is made herein. The other of these is to attach a piece or fragment to the drug that allows formation of —CNO. One method of carrying out the latter is via a bromoketone to link via ether, amine or ester. Instead of using a bromoketone, a carboxylic acid derivative can be reacted with hydroxy group or amine group of a conventional drug to obtain an amide or ester linkage.

The Compound (129a) can be prepared by the following route of synthesis:

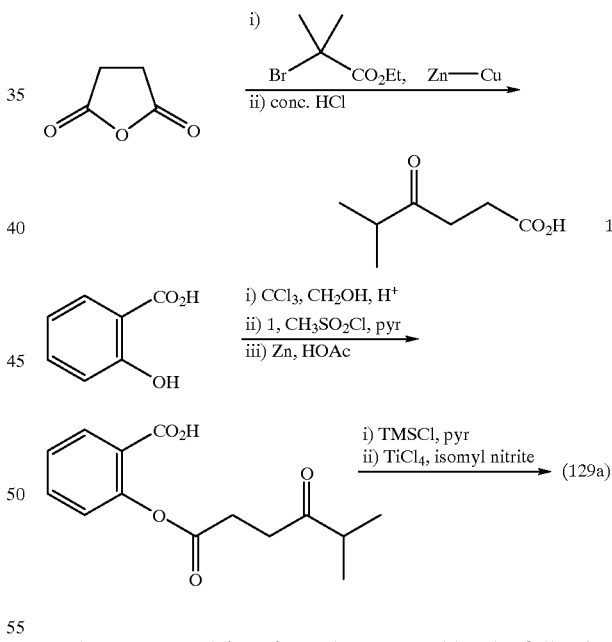

The Compound (130a) can be prepared by the following route of synthesis:

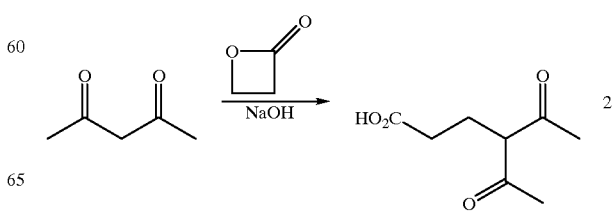

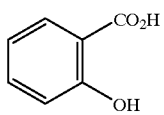 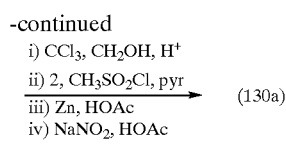 (130a)

i) CCl₃, CH₂OH, H⁺
ii) 2, CH₃SO₂Cl, pyr
iii) Zn, HOAc
iv) NaNO₂, HOAc

We turn now to utility of the C-nitroso compounds of the first embodiment herein.

The C-nitroso compounds of the first embodiment herein have utility as NO donors and in such function provide relaxation and platelet inhibiting effect. Thus, C-nitroso compounds of the first embodiment herein are useful to prevent restenosis following angioplasty in patients at risk for restenosis following angioplasty and to inhibit platelets to prevent coagulation and to treat angina in patients at risk for coagulation and thrombus formation. The NO donor function also provides the following therapeutic effects: inhibition of microbes and treatment of impotence, asthma, heart failure, stroke, arthritis, ARDS, cancer and any pathological proliferation of cells and any NMDA related injury.

As indicated above, the C-nitroso compounds of the first embodiment herein with high NO-donating capacity (from carbon acids with pKa's less than about 10) exhibit weak (micromolar concentration) effects, probably through nitrite and are potentiated by added glutathione or similar low molecular weight thiols. These compounds cause formation of nitrosoglutathione and are therefore especially useful to treat patients in need of nitrosoglutathione, e.g., patients with cystic fibrosis, asthma, hypoxia and ischemic disorders.

As indicated above, the C-nitroso compounds of the first embodiment herein with weak NO-donating capabilities (from carbon acids with pKa's ranging from about 15 to about 20) show high activities through specific nitrosylation of strongly nucleophilic targets and are therefore useful to nitrosylate thiols in proteins in highly nucleophilic milieus and thus are useful to treat patients in need of nitrosylated proteins, e.g., patients with hypertension, neurodegeneration and painful crisis of sickle cell disease.

When C-nitroso compounds of the first embodiment herein are derived from nonsteroidal anti-inflammatory drugs that inhibit COX-1 as well as COX-2, the C-nitroso compounds are useful to treat inflammatory or painful disorders including arthritis, coronary artery disease and urinary incontinence and improve the profile of selective inhibitors of COX-2, e.g., in the treatment of angina. The nitrosoketoibuprofen prepared herein has these utilities.

As indicated above and will be discussed in more depth in the description of advantages below, the stability of the dimeric form of isolated C-nitroso compounds of the first embodiment herein improves compound lifetime and provides modulated bioactivity. This characteristic permits their use as sustained release drugs. Such stability also connotes utility as prodrugs. Because spontaneous release of NO is both controllable and small, many C-nitroso compounds will be active only in the presence of small molecule activators, e.g., low-molecular weight thiols acting as carriers of NO (in an appropriate redox form) from the C-nitroso compound to a biological target.

Moreover, C-nitroso compounds of the first embodiment herein can be incorporated into polymers for coatings on medical devices. In the case of such coatings, polymerizable C-nitroso compounds can be copolymerized with appropriate monomers to yield plastics or elastomers as desired.

The polymers into which C-nitroso compounds of the first embodiment herein can be incorporated include all biocompatible polymers, including PVP and PVP-urethane copolymers; hydrogels; polylactides and polylactide-co-polyethyleneglycol; polyacrylonitriles, polyacrylonitrile/polyacrylamide/ polyacrylic acid copolymers; polyurethanes, polycarbonates, polyethers and copolymers of the three; silicone polymers and copolymers; carbohydrate polyacrylonitrile/polyacrylamide/ polyacrylic acid copolymers; polyurethanes, polycarbonates, polyethers and copolymers of the three; silicone polymers and copolymers; carbohydrate polymers, including starches and modified starches, cellulose and cellulosidic materials, chitin and chitosan, glycosamine glycans, including hyaluronic acid, chondroitin and chondroitin sulfate, wherein the polymer has been modified to incorporate C-nitroso moieties derived from carbon acids with pKa values less than about 25. The C-nitroso moieties can be bound as esters or ethers to pendant hydroxyl groups, as esters to pendant carboxylic acids or as amines or amides to pendant amino moieties. The nitrosylated polymer itself can be prepared in a variety of ways. Nitrosylated monomers can be incorporated into a growing polymer during either a free radical, ionic, metathesis or living polymerization. Alternatively, a completed polymer can be derivatized following synthesis to incorporate the above listed residues by treating, for example, hydroxylated or amine-containing polymers with carboxylic acid chlorides or alkyl halides, carboxylate-containing polymers with alkyl halides. Finally, a C-nitroso precursor, for example, a monomer containing a dione or a vinyl silane can be polymerized into a growing polymer chain by a free radical, ionic, metathesis or living polymerization and then nitrosylated following polymerization by exposure to a source of nitrosonium, for example acidified nitrite, titanium tetrachloride and an alkyl nitrite, respectively.

Said polymers, can have weight average molecular weights (determined by light scattering) ranging, for example, from 50,000 to 500,000.

We turn now to dosages and methods of administration for the C-nitroso compounds of the first embodiment herein when they are used for therapeutic utility, using part of it as the C-nitroso derivative. The reason for the wide range is that many compounds are embraced by the invention.

Routes of administration include, for example, oral, parenteral including intravenous, inhaled, nebulized, and topical.

When the C-nitroso compound of the first embodiment herein is derived from a conventional drug, the dosages utilized are those in use for the conventional drug and the methods of use are those for the conventional drug but, as indicated above, only part of the drug is administered as the C-nitroso compound with the rest being administered as the conventional drug, if necessary.

When the C-nitroso compound is one obtained by nitrosylation of a carbon acid having a pKa less than about 10, it is preferably administered in a concentration ranging from 1 nanomolar to 100 micromolar as an aqueous solution unless potentiation is provided by glutathione or other low-molecular weight thiol whereupon the C-nitroso compound is preferably administered in a concentration ranging from 1 to 900 nanomolar and the glutathione is administered in a concentration ranging from 1 micromolar to 100 millimolar.

When the C-nitroso compound is one that is obtained from a carbon acid having a pKa ranging from about 15 to about 20, the C-nitroso compound is preferably administered in a concentration ranging from about 1 nanomolar to 100 micromolar.

We turn now to the ibuprofen derivative, i.e., dimeric 2-[4'-(α-nitroso)isobutyrylphenyl]propionic acid. It is preferably administered as a pill, tablet or capsule or the like, with only part of the ibuprofen being administered as the C-nitroso derivative, e.g., one part by weight ibuprofen derivative, to 1,000 parts by weight underivatized ibuprofen to provide 400 mg on an ibuprofen basis, three to four times day and from 1 nanomolar to 100 micromolar C-nitroso compound concentration.

The compounds of the first embodiment herein are advantageous over the C-nitroso compounds known heretofore in activity and/or in solubility.

We turn now to the advantages of the C-nitroso compounds of the first embodiment herein over O-nitroso compounds and S-nitroso compounds as NO donors.

A major barrier to use of organic nitrites and nitrosothiols as NO (or nitrosonium) donors is their instability. For example, nitrosothiols undergo rapid decomposition to yield inter alia nitric oxide radical and a sulfur radical. In contrast, C-nitroso compounds of the first embodiment undergo a dimerization reaction to produce a solid, stable dimer. As indicated above, this dimerization reaction proceeds spontaneously during isolation of C-nitroso compounds and the dimerization is greatly favored for α-acyl C-nitroso compounds. In general, the dimers are solid and stable, capable of being stored at ambient temperature in the presence of oxygen and light for months. The C-nitroso compounds herein have a significant advantage over O-nitroso and S-nitroso compounds of the first embodiment from the standpoint of shelf stability.

The C-nitroso compounds of the first embodiment herein are also advantageous over O-nitroso and S-nitroso compounds as NO donors in that their functionality, i.e., NO donating potential and reactivity, can be tailored, while this is not the case for O-nitroso and S-nitroso compounds.

We turn firstly to tailoring the NO donating potential of C-nitroso compound of the first embodiment herein. This can be done in three ways. Firstly, the rate of transfer of nitrosonium equivalent is directly proportional to acidity. Thus, NO donating potential is increased by obtaining C-nitroso compound from starting material with lower pKa. Secondly, the NO donating potential is related to the position (equilibrium constant) of the dimer-monomer equilibrium (thermodynamics). This property is because, as indicated above, the dimer is stable and inactive whereas the monomer is active. Thirdly, the NO donating potential is influenced by the rate of interconversion of the dimer and monomer (kinetics). This feature can be utilized, for example, by positioning an acyl alpha to the nitroso carbon to slow down the rate of interconversion to monomer. On the other hand, the NO-donating capability of organic nitrites and nitrosothiols is largely a function of the heteroatom (oxygen or sulfur); there is little in the way of relationship between structure and activity.

We turn now to tailoring of the reactivity of C-nitroso compounds. This can be accomplished sterically or electronically. We turn now to the steric tailoring of reactivity. The addition of steric bulk at the α-carbon slows transfer of a nitrosonium equivalent. Thus, for example, highly hindered protein sulphydryl receptors can be protected against S-nitrosylation through use of highly hindered C-nitroso donors. We turn now to electronic tailoring of reactivity. Firstly, the rate of transfer of nitrosonium equivalent is directly proportional to the acidity of the parent carbon acid. Secondly, the reactivity can be tailored by selecting starting material with groups that can tailor donating potential. For example, addition of groups such as acyl and electronegative substituents, will lower the acidity of the carbon acid and in turn enhance the NO$^+$ donating capacity of the C-nitroso compound. Moreover, alteration of groups changes the form of nitric oxide liberated. The alteration of groups can change the acidity as much as $10^{40}$, greatly exceeding the range available with sulfur or oxygen-based conjugates.

Methods for providing different groups in C-nitroso compound are available in the methods of synthesis described above where bromomethylketone derivatives of either 3-nitroso-2,4-pentanedione on 4-nitroso-2,3-butadione are used and these groups can influence the monomer-dimer properties and NO-donating potential of the final product.

We turn now to the C-nitroso compounds of the second embodiment herein. These contain the moiety

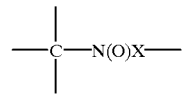

where X is S, O or NR where R is selected from the group consisting of $C_1$–$C_6$ alkyl which is unsubstituted or which is substituted with one or more alcohol, ether; ester or amide groups which contain from 2 to 10 carbon atoms; and has a molecular weight ranging, for example, from about 100 to about 1,000.

A preferred subgenus of the second embodiment herein comprise the structure:

(135)

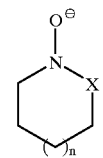

where X is S, O or NR where R is as defined for the genus of the second embodiment and n ranges from 0 to 4 and the corresponding protonated compounds (instead of existing with the negative charge).

The structure (135) may be substituted with $C_1$–$C_6$ alkyl or $C_{1-6}$ alkyl carbonyl and includes the modification that the carbon pendant to X and a carbon within the parentheses can also be part of another ring. For example, a compound of the second embodiment herein is:

(135a)

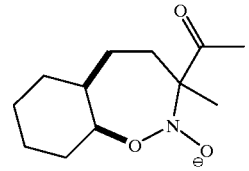

The compounds of the second embodiment form spontaneously from corresponding C-nitroso compounds that contain alcohol thiol or amine. For example, the Compound (135a) is formed by the following route of synthesis:

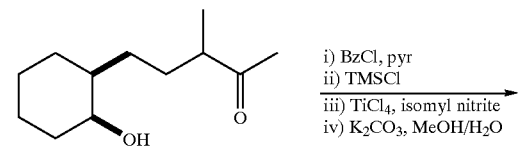

i) BzCl, pyr
ii) TMSCl
iii) TiCl$_4$, isomyl nitrite
iv) K$_2$CO$_3$, MeOH/H$_2$O

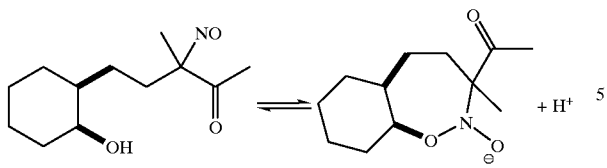

where Bz stands for benzoyl.

The compounds of the second embodiment herein have utility as NO donors as described above in conjunction with the C-nitroso compounds of the first embodiment and are used with the dosage ranges and routes of administration described in conjunction with the C-nitroso compounds of the first embodiment and are characterized by similar stability to the dimers of the C-nitroso compounds of the first embodiment.

We turn now to the embodiment herein directed to inhibitors of COX-2 where a tertiary carbon on an oxygen or a sulfur is nitrosylated.

Examples of inhibitors of COX-2 where a tertiary carbon is nitrosylated are compounds (115)–(128) set forth above.

Examples of inhibitors of COX-2 where an oxygen or sulfur is nitrosylated include, for example, derivatives of Celebrex, indomethacin, L-745,337, and etudolac.

Examples of compounds derived from Celebrex include the following:

(200)
(201)

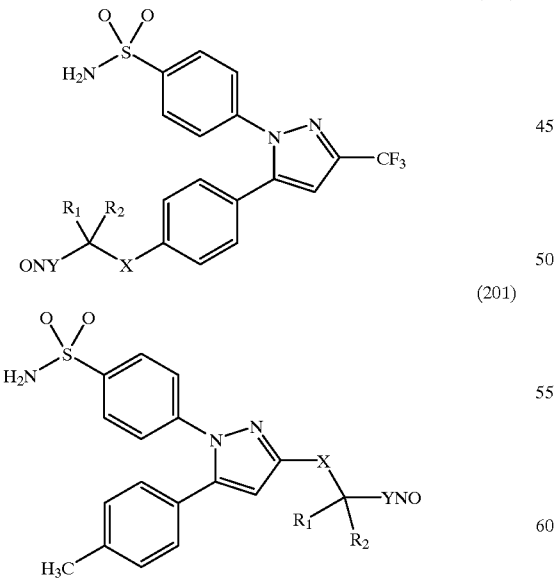

Examples of compounds derived from indomethacin include the following:

(202)
(203)

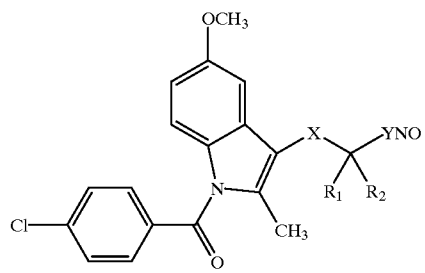

An example of a compound derived from L-745,337 is (204)

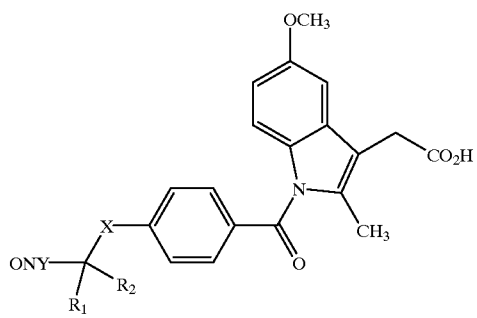

Examples of compounds derived from etudolac include the following:

(205)
(206)

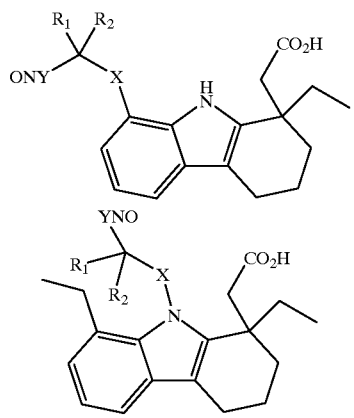

In the compounds (200), (201), (202), (203), (204), (205) and (206), Y is S or O; $R_1$ and $R_2$ are H or $C_1$–$C_6$ alkyl; and X is $C_1$–$C_6$ alkyl $C_6$–$C_{20}$ aryl and substituted derivatives thereof, e.g., substituted with amino, hydroxyl, and/or carboxy and/or which are sulfated and/or phosphorylated.

The COX-2 inhibitor compounds which are O-nitrosylated are obtained from the parent alcohol by treatment with an appropriate nitrosylating agent, e.g., acidified nitrite, nitrosyl chloride, nitrosyl bromide, nitrosonium perchlorate, nitrosonium hydrogen sulfate or nitrosonium tetrafluoroborate.

The COX-2 inhibitor compounds which are S-nitrosylated are obtained from the parent thiol by treatment with an appropriate nitrosating agent, e.g., those set forth in the paragraph directly above or alkyl nitrite.

The dosage on a COX-2 inhibitor basis is the same as the dosage for the underivatized COX-2 inhibitor. To effect this, only part of the COX-2 inhibitor can be administered in the form of nitrosylated compound. The route of administration is the same as for the underivatized COX-2 inhibitor.

The invention is illustrated by the following working examples.

EXAMPLE I

Synthesis of Dimeric 2-[4'-(α-Nitroso) isobutyrylphenyl]propionic Acid

The synthesis of dimeric 2-[4'-(α-nitroso) isobutyrylphenyl]propionic acid was carried out according to the reaction scheme for this set forth above as follows:

To a solution of ibuprofen 1A (9.89 g, 48 mmol) in anhydrous EtOH (35 mL) was added chlorotrimethylsilane (18.27 mL, 144 mmol) at room temperature, and the mixture was stirred at the same temperature for 2h. After the removal of the excess EtOH and chlorotrimethylsilane under reduced pressure, the oily residue was treated with ice-cold saturated $NaHCO_3$ (150 mL), and the resulting mixture was extracted with hexanes (450 mL). The hexanes solution was washed with brine (3×50 mL), and dried over anhydrous $Na_2SO_2$. Evaporation of the solvent afforded ethyl 2-(4'-isobutylphenyl)propionate 2A (11.24 g, in 100% yield) as a colorless oil.

Ester 2A (11.23 g, 48 mmol) was added dropwise to a stirred suspension of $CrO_3$ (20.8 g, 208 mmol) in acetic acid (AcOH) (34 mL) and $H_2O$ (1.1 mL) within 30 min, maintaining the reaction temperature at 45–55° C. After the completion of addition, the mixture was stirred for 20 min, and then the mixture was heated with stirring at 50–55° C. for additional 85 min, giving a blue-black suspension. The AcOH was removed under reduced pressure, and the residue solid was suspended in ice-cold $H_2O$ (400 mL), and extracted with EtOAc (450 mL). The extract was washed with brine (5×50 mL), and dried ($Na_2SO_4$). The crude products were purified by flash chromatography (eluting with 7% EtOAc in hexanes) to give unreacted ester 2A (2.78 g), followed by ethyl 2-(4'-isobutyrylphenyl)propionate 3a (4.3 g, 48% yield based on consumed 2A) as a light-yellow oil.

Fifteen percent aqueous NaOH (10 mL) was added to a solution of 3A (3.2 g, 12.9 mmol) in MeOH (150 mL), and stirred at room temperature for 2 h. After the removal of the MeOH by evaporator, the dark-brown residue was treated with ice-cold 2M HCl (100 mL), and the resulting grey-white suspension was extracted with EtOAc (400 mL), and finally dried ($Na_2SO_4$). Flash chromatographic purification of the crude products (eluting with 60% EtOAc in hexanes) afforded 2-(4'-isobutyrylphenyl)propionic acid 4a (2.5 g, 88% yield) as an amorphous solid.

To a stirred mixture of 4A (1.59 g, 7.2 mmol) and triethylamine (3.03 mL, 21.7 mmol) was added chlorotrimethylsilane (2.75 mL, 21.7 mmol) at room temperature, and then a solution of sodium iodide (3.26 g, 21.7 mmol) dissolved in anhydrous acetonitrile (25 mL) was introduced in one portion. The mixture was stirred at room temperature for 8 h, then extracted with hexanes (400 mL). The hexanes extract was washed with ice-cold brine (2×30 mL), and dried ($Na_2SO_4$). Concentration of the solvent afforded trimethylsilyl 2-[4'-(1-trimethylsiloxy-1-isobutenyl)phenyl] propionate 5A (2.08 g, 79% yield) as a viscous oil, which was used without further purification.

A solution of 5A (2.1 g, 5.7 mmol) dissolved in anhydrous $CH_2Cl_2$ (25 mL) was cooled to −10° C. Isoamyl nitrite (2.4 mL, 17.6 mmol) was added in one portion, then 1M $TiCl_4$ $CH_2Cl_{12}$ solution (13.0 mL, 13.0 mmol) was added dropwise at −10° C. within a period of 20 min. After stirring at the same temperature for additional 60 min, the resulting deep-green mixture was poured into ice-cold $H_2O$ (100 mL), and stirred for 5–10 min, then extracted with EtOAc (400 mL), and finally dried ($Na_2SO_4$). Evaporation of the solvent under reduced pressure gave an amorphous solid, which was suspended in $CH_2Cl_2$ (50 mL) and collected by filtration. The white solid was washed with additional $CH_2Cl_2$ (3×10 mL) to give dimeric 2-[4'-(α-5 nitroso)isobutyrylphenyl] propionic acid 6A (0.75 g, 53% yield).

EXAMPLE II

The ability of various C-nitroso compounds as described below to relax a rabbit aortic ring (smooth muscle) was carried out as described in Stamler, J., et al., PNAS, Vol. 89, 444–448 (1992).

Results shown in FIGS. 1–10 which are tracings of force (tension) in the Y-direction versus time in the X-direction with downward direction indicating relaxation and upward direction indicating constriction. Concentrations of C-nitroso compound applied at time in the X-direction are indicated as $10^9$ (1 nanomolar), $10^6$ (1 micromolar), $10^3$ (1 milimolar), etc. "PE" on the figures means the application of phenylephrine, a constricting agent.

FIG. 1 shows results for Compound (129a) which is a C-nitroso compound obtained by nitrosylating a carbon acid with a pH less than 10. Relaxation effect is shown in FIG. 1 at 10 μM concentration, i.e., at micromolar concentrations.

Figure 2:
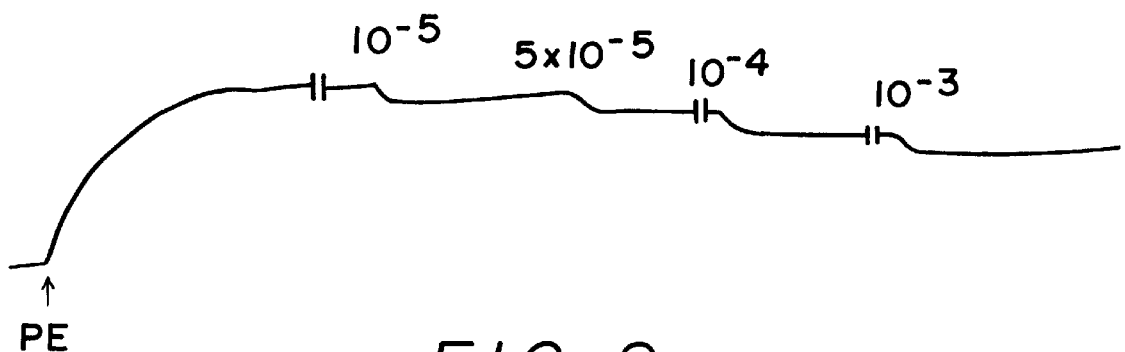

FIG. 2 shows results for C-nitroso-methylmalonic acid. It is obtained from a carbon acid with a pKa of about 30–35. As shown in FIG. 2, it displays relaxation effect at 10 micromolar concentration (very weak activity).

Figure 3:
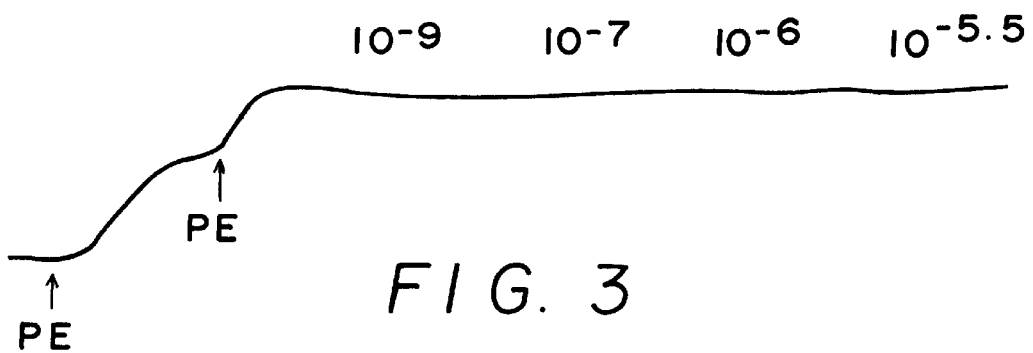

FIG. 3 shows results for C-nitrosobenzene. It is obtained from a carbon acid having a pKa of about 45. As shown in FIG. 3, it displays no activity at micromolar concentration.

Figure 4:
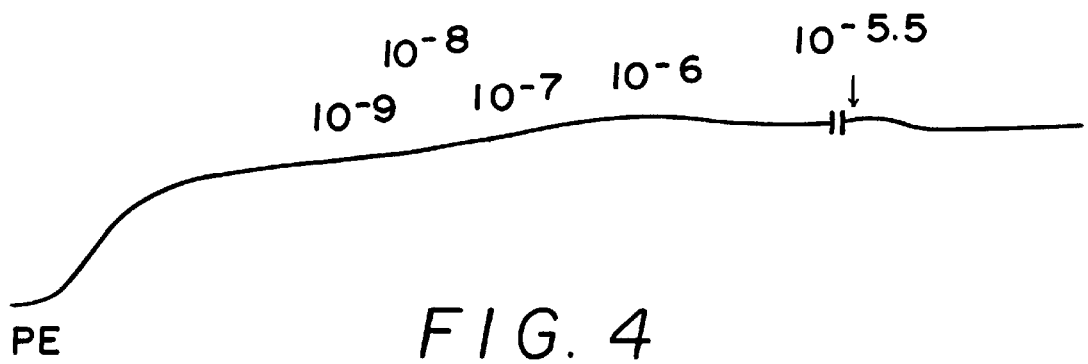

FIG. 4 shows results for C-nitrosophenol. C-Nitrosophenol is obtained from a carbon acid having a pKa greater than 25. As shown in FIG. 4, it displays no activity at micromolar concentrations.

Figure 5:
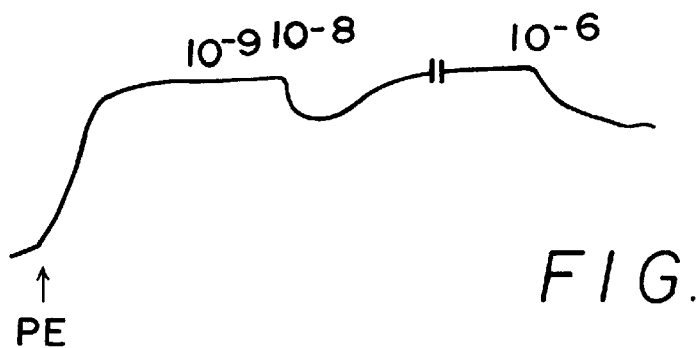

FIG. 5 shows results for the nitrosoketoibuprofen synthesized in Example I. As shown in FIG. 5, it displays relaxation effect at 10 nanomolar concentration.

Figure 6:
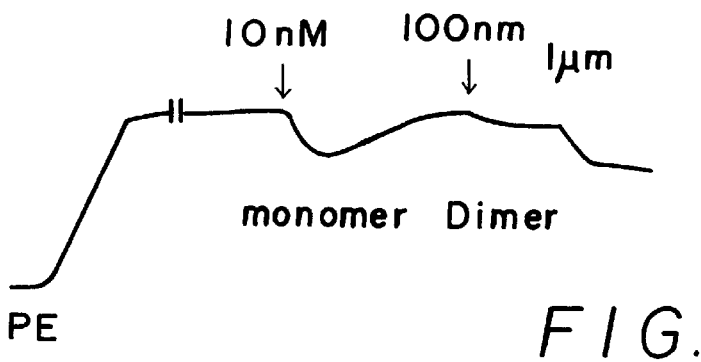

FIG. 6 shows further results for the nitrosoketoibuprofen synthesized in Example I. FIG. 6 shows the same relaxation effect at 10 nanomolar as does FIG. 7 but not much more activity at higher concentration (since the equilibrium moves in the direction of inactive dimer at higher concentrations).

Figure 7:
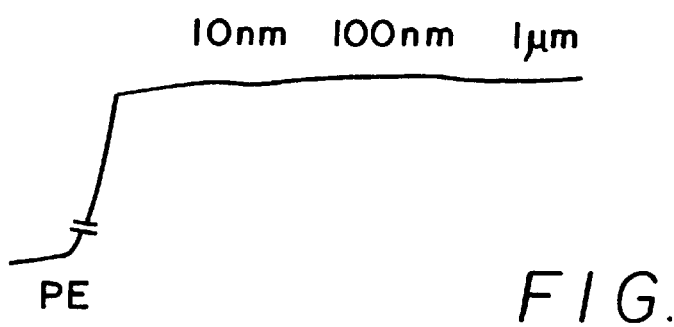

FIG. 7 shows results for the nitrosoketoibuprofen synthesized in Example I used in conjunction with 100 μM glutathione. As shown in FIG. 7, there is no activity because glutathione blocks the activity of the nitrosoketoibuprofen by complexing with it to tie up the NO group (the same occurrence as for dimer); this is a reflection of the C—N (O)R group described above.

Figure 8:
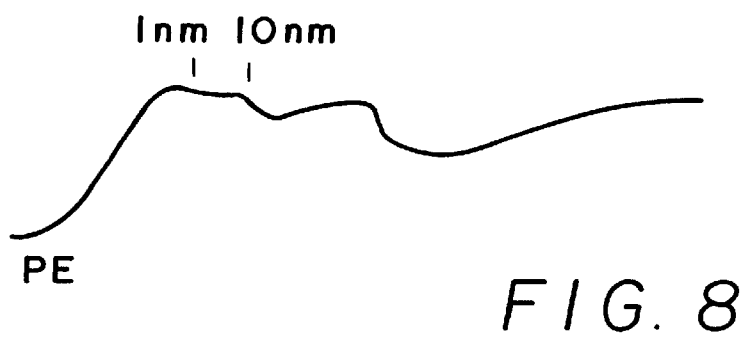

FIG. 8 shows more results for the nitrosoketoibuprofen synthesized in Example I. Relaxation is shown at 1 and 10 nM concentration. This differs some from what is shown in FIGS. 5 and 6 because of the natural variability among blood vessels.

Figure 9:
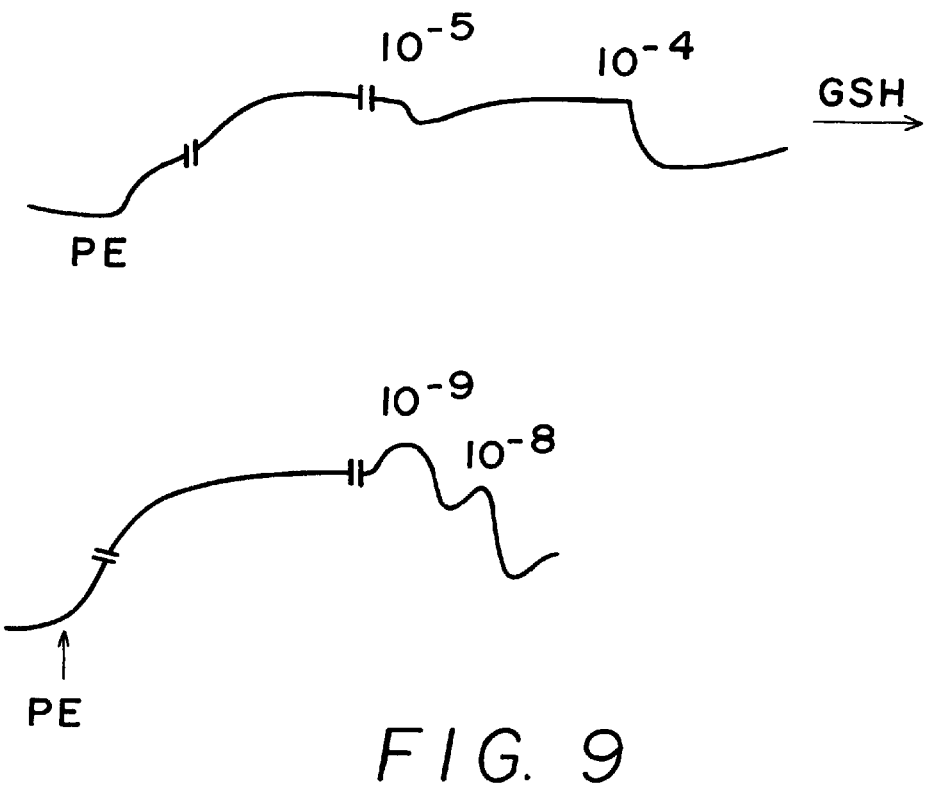

FIG. 9 shows results for 3-methyl-3-nitroso-2,4-petanedione which is obtained from a carbon acid with a pKa less than 10. This compound is not water soluble. It displays relaxation effect at concentration greater than 10 micromolar and further effect at concentration greater than 100 micromolar, but when 100 μM glutathione is added it displays relaxation effect at between 1 and 10 nanomolar concentration. The potentiation effect occurs because the C-nitrosodione reacts with glutathione to form S-nitrosoglutathione.

Figure 10:
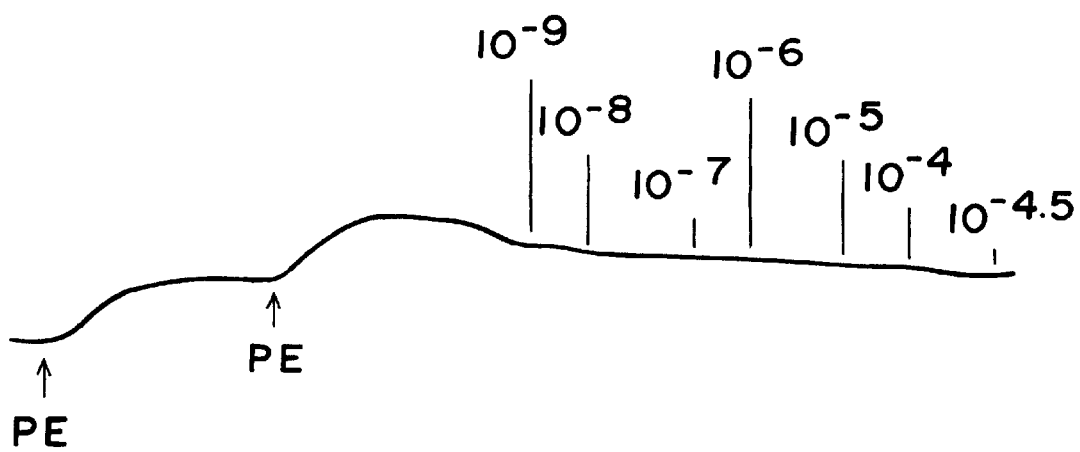

FIG. 10 shows results for 2-methyl-2-nitrosopropane. It is obtained from a carbon acid having a pKa of about 55 and is not water soluble. It displays no relaxation effect activity at any of the concentrations used.

EXAMPLE III

A 60-year-old white male with arthritis, esophageal spasm, coronary artery disease, congestive heart failure, impotence and nightly urinary incontinence develops gastrointestinal upset when administered ibuprofen (400 mg, three times a day). When the drug is changed so that 0.1% by weight of the drug is administered as the dimeric nitrosoketoibuprofen of Example I, all symptoms are relieved.

EXAMPLE IV

A 65-year-old male with angina treated with nitroglycerin develops nitrate tolerance. Nitroglycerin administration is stopped and Compound (135a) is given at 20 μg/min continuously with relief of angina.

EXAMPLE V

A 62-year-old white male with severe rheumatoid arthritis presents with myocardial infarction. His nonsteroidal anti-inflammatory drug is stopped because of concerns of increased cardiovascular risk. His joint pain becomes debilitating. Celebrex is administered orally twice a day in 200 mg amount except that 0.1% by weight of the drug is administered as Compound (115) where $R_1$ and $R_2$ are methyl, with relief of both joint pain and angina.

When Compound (200) where $R_1$ and $R_2$ are H and X is —$CH_2$—, and Y is S or O is substituted for the Compound (115) in equal amount, relief of both joint pain and angina is also obtained.

Variations

Variations of the above will be obvious to those skilled in the art. Thus, the scope of the invention is defined by the claims.

What is claimed is:

1. A C-nitroso compound having a molecular weight ranging from 225 to 1,000 on a monomeric basis, wherein a nitroso group is attached to a tertiary carbon, which is obtained by nitrosylation of a carbon acid having a pKa less than about 25, wherein a substituent Q is attached to the tertiary carbon and consists of a chain moiety containing from 1 to 12 chain atoms consisting of 1 to 10 carbon atoms, 0 to 2 nitrogen atoms, and 0 to 2 oxygen atoms covalently bonded to a cyclic moiety which is monocyclic, bicyclic, tricyclic, tetracyclic or pentacyclic, and contains 5 to 24 ring atoms consisting of 2 to 20 carbon atoms, 0 to 4 nitrogen atoms, 0 to 1 oxygen atoms and 0 to 1 sulfur atoms.

2. The C-nitroso compound of claim 1 which is water-soluble.

3. The C-nitroso compound of claim 2, where the tertiary carbon is attached to at least one carbonyl group.

4. The C-nitroso compound of claim 3 which has a molecular weight ranging from 225 to 600 on a monomeric basis.

5. The C-nitroso compound of claim 4 which is obtained by nitrosylation of a carbon acid having a pKa less than about 10.

6. The C-nitroso compound of claim 4 which is obtained by nitrosylation of a carbon acid having a pKa ranging from about 15 to about 20.

7. A C-nitroso compound as defined in claim 1 which is obtained by nitrosylating a tertiary carbon of a therapeutic agent without NO donor effect or of said agent modified to modify the carbon acid pKa thereof.

8. A C-nitroso compound as defined in claim 2 which is obtained by nitrosylating a tertiary carbon of a therapeutic agent without NO donor effect or of said agent modified to modify the carbon acid pKa thereof.

9. A C-nitroso compound as defined in claim 3 which is obtained by nitrosylating a tertiary carbon of a therapeutic agent without NO donor effect or of said agent modified to modify the carbon acid pKa thereof.

10. A C-nitroso compound as defined in claim 4 which is obtained by nitrosylating a tertiary carbon of a therapeutic agent without NO donor effect or of said agent modified to modify the carbon acid pKa thereof.

11. A C-nitroso compound as defined in claim 5 which is obtained by nitrosylating a tertiary carbon of a therapeutic agent without NO donor effect or of said agent modified to modify the carbon acid pKa thereof.

12. A C-nitroso compound as defined in claim 6 which is obtained by nitrosylating a tertiary carbon of a therapeutic agent without NO donor effect or of said agent modified to modify the carbon acid pKa thereof.

13. A C-nitroso compound having a molecular weight ranging from 225 to 600 on a monomeric basis wherein a nitroso group is attached to a tertiary carbon which is obtained by nitrosylation of a nonsteroidal anti-inflammatory drug having a carbon acid pKa ranging from about 15 to about 20 or a nonsteroidal anti-inflammatory drug modified to have a carbon acid pKa ranging from about 15 to about 20.

14. A C-nitroso compound as defined in claim 13 which is obtained by nitrosylation of ibuprofen modified to have a carbon acid pKa ranging from about 15 to about 20.

15. A method of treating a patient with an inflammatory or painful disorder which is treatable with a nonsteroidal anti-inflammatory drug comprising administering to said patient a therapeutically effective amount of a compound as defined in claim 13 or an aqueous solution thereof.

16. A method of treating a patient with an inflammatory or painful disorder which is treatable with ibuprofen comprising administering to said patient a therapeutically effective amount of a compound as defined in claim 14 or an aqueous solution thereof.

17. A method of treating a patient in need of nitrosoglutathione which comprises administering to said patient a therapeutically effective amount of a compound as claimed in claim 5 optionally with administration of glutathione.

18. A COX-2 inhibitor where a tertiary carbon atom is nitrosylated, said COX-2 inhibitor having a molecular weight ranging from 225 to 1,000 on a monomeric basis.

19. A C-nitroso compound as defined in claim 1 which is:

(1)

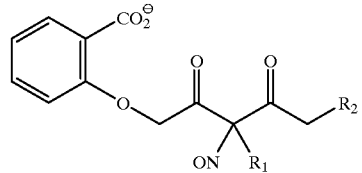

where the balancing cation is a hydrogen ion and where $R_1$ and $R_2$ are selected from the group consisting of $C_1$–$C_6$ alkyl and $C_6$–$C_{20}$ aryl and these substituted with substituent selected from the group consisting of amino, hydroxyl and carboxy.

* * * * *